US010302586B2

(12) United States Patent
Sun et al.

(10) Patent No.: US 10,302,586 B2
(45) Date of Patent: May 28, 2019

(54) STRETCHABLE IONICS FOR TRANSPARENT SENSORS AND ACTUATORS

(71) Applicant: President and Fellows of Harvard College, Cambridge, MA (US)

(72) Inventors: Jeong Yun Sun, Cambridge, MA (US); Christoph Matthias Keplinger, Cambridge, MA (US); Zhigang Suo, Lexington, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 554 days.

(21) Appl. No.: 14/768,850

(22) PCT Filed: Apr. 10, 2014

(86) PCT No.: PCT/US2014/033646
§ 371 (c)(1),
(2) Date: Aug. 19, 2015

(87) PCT Pub. No.: WO2014/169119
PCT Pub. Date: Oct. 16, 2014

(65) Prior Publication Data
US 2016/0025669 A1     Jan. 28, 2016

Related U.S. Application Data

(60) Provisional application No. 61/810,466, filed on Apr. 10, 2013.

(51) Int. Cl.
*G01L 1/14* (2006.01)
*G01N 27/30* (2006.01)
(Continued)

(52) U.S. Cl.
CPC .......... *G01N 27/305* (2013.01); *G01N 27/02* (2013.01); *G01N 27/3335* (2013.01); *H01G 9/022* (2013.01)

(58) Field of Classification Search
CPC .. G01N 27/305; G01N 27/02; G01N 27/3335; G01N 27/223; G01N 27/403;
(Continued)

(56) References Cited

U.S. PATENT DOCUMENTS 5,661,629 A * 8/1997 MacFarlane ........... H01G 9/025
                                                                  361/503
5,748,439 A * 5/1998 MacFarlane ............. H01G 9/02
                                                                  361/502

(Continued)

OTHER PUBLICATIONS

Dubois et al., "Microactuators based on ion implanted dielectric electroactive polymers (EAP) membranes," Sensors and Actuators A, 130-131, (2006), pp. 147-154.
(Continued)

*Primary Examiner* — Lisa M Caputo
*Assistant Examiner* — Nigel H Plumb
(74) *Attorney, Agent, or Firm* — Wilmer Cutler Pickering Hale and Dorr LLP

(57) ABSTRACT

A class of devices enabled by ionic conductors is highly stretchable, fully transparent to light of all colors, biocompatible or biodegradable, and capable of operation at frequencies beyond 10 kilohertz and voltages above 10 kilovolts. These devices enabled by ionic conductors can be used as large strain actuators, full-range loudspeakers, as strain or pressure sensors and as stretchable interconnects. The electromechanical transduction is achieved without electrochemical reaction. When large stretchability and high optical transmittance are required, the ionic conductors have lower sheet resistance than all existing electronic conductors.

24 Claims, 25 Drawing Sheets

(51) Int. Cl.
*H01G 9/022* (2006.01)
*G01N 27/02* (2006.01)
*G01N 27/333* (2006.01)

(58) Field of Classification Search
CPC .......... H01G 9/022; H01G 9/02; G01L 1/142; G01B 7/16; G01B 7/18; G01B 5/30; H01B 1/20; G02F 1/153
See application file for complete search history.

(56) References Cited

U.S. PATENT DOCUMENTS

| | | | |
|---|---|---|---|
| 6,343,129 B1* | 1/2002 | Pelrine | F04B 35/045 381/116 |
| 7,062,055 B2 | 6/2006 | Pelrine et al. | |
| 7,834,527 B2* | 11/2010 | Alvarez Icaza Rivera | H01L 41/0478 310/344 |
| 7,951,186 B2* | 5/2011 | Eidenschink | A61L 29/146 623/1.11 |
| 2011/0198222 A1* | 8/2011 | Bhatia | G01N 27/07 204/403.01 |
| 2012/0224247 A1* | 9/2012 | Sotzing | H01M 4/02 359/265 |
| 2012/0241689 A1* | 9/2012 | Itou | H01B 1/22 252/511 |

OTHER PUBLICATIONS

Niu et al., "Synthesizing a New Dielectric Elastomer Exhibiting Large Actuation Strain and Suppressed Electromechanical Instability without Prestretching," Journal of Polymer Science, Polymer Physics, vol. 51, pp. 197-206, (2013).
Pelrine et al., "High-Strain Actuator Materials Based on Dielectric Elastomers," Advanced Materials, vol. 12, No. 16, pp. 1223-1225, Aug. 16, 2000.
Rosset et al., "Ion-implanted compliant and patternable electrodes for miniaturized dielectric elastomer actuators," Proc. of SPIE vol. 6927 69270W-1, (2008), 11 pages.
Rosset et al., "Mechanical properties of electroactive polymer microactuators with ion implanted electrodes," Proc. of SPIE vol. 6524 652410-1, (2007), 12 pages.
Sun et al., "Highly stretchable and tough hydrogels," Nature, vol. 489, pp. 133-136, Sep. 6, 2012.
International Search Report and Written Opinion issued by the U.S. Patent and Trademark Office as International Searching Authority for International Application No. PCT/US14/33646 dated Aug. 21, 2014 (9 pages).

* cited by examiner 120    110

Voltage off

Voltage on

Voltage off

Voltage on

Voltage off

Voltage on

FIG. 8A          FIG. 8B
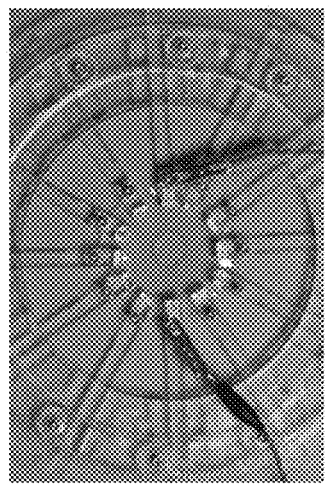 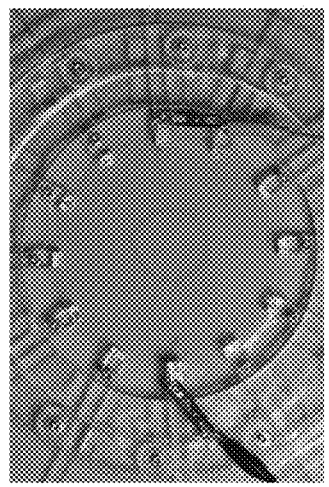
FIG. 8C
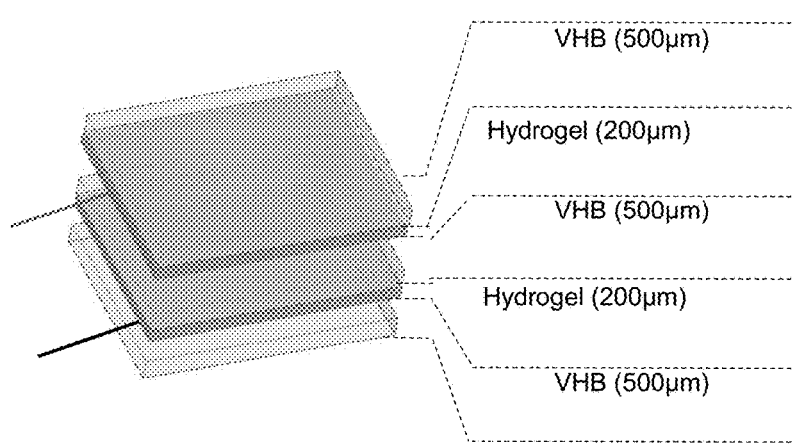

STRETCHABLE IONICS FOR TRANSPARENT SENSORS AND ACTUATORS

CROSS-REFERENCE TO RELATED APPLICATIONS

This application is a national stage application of International Application No. PCT/US14/033646 filed on Apr. 10, 2014 which claims benefit under 35 U.S.C. § 119(e) of the earlier filing date of U.S. Provisional Patent Application No. 61/810,466, filed on Apr. 10, 2013, entitled "Stretchable Ionics: Ultra-Transparent Electrodes Capable of Operation at High Frequency and Voltage," which is hereby incorporated by reference.

STATEMENT REGARDING FEDERALLY SPONSORED RESEARCH

The present invention was made with United States government support under Grant No. DMR-0820484 awarded by National Science Foundation, Grant No. W911Nf-09-1-0476 awarded by the United States Army and under Grant No. DE-FG02-00ER45852 awarded by the Department of Energy. The United States government has certain rights in this invention.

INCORPORATION BY REFERENCE

All patents, patent applications and publications cited herein are hereby incorporated by reference in their entireties in order to more fully describe the state of the art as known to those skilled therein as of the date of the invention described herein.

BACKGROUND

In nature electric signaling is based on ionic conductors. The human brain sends electrical impulses (action potentials) through the axons of neurons to control muscle contraction. Sensory neurons convert external stimuli like pressure or temperature changes into electric signals that are sent to the brain—all mediated by the movement of ions. In contrast to nature modern electrical devices are largely based on electronic conductors, mainly metals. Distributing electrical power for lighting, heating and powering machines necessitates high current densities where metals like copper, aluminum, silver or gold excel with superior conductivity. The free electrons in the conduction band of metals allow for ultra-high frequencies in modern computation and communication devices.

Inspired by an increasing interest to extend the use of electronics to circuits on flexible and stretchable substrates (sensor skins for soft machines), interfacing electronics with life, research has yielded ingenious solutions to make metal stretchable. Most commonly used are combinations of elastomeric substrates with gold/copper/etc. conductors on top that form meanders, buckling wave structures, and bridges. Also used are conducting particles inside an elastomeric matrix where conductivity is based on percolation.

Nonetheless, metals are problematic when conductors are required to be transparent. Indium tin oxide (ITO) is used for many applications, where flexibility is not required. Carbon nanotubes, silver nanowires and graphene on elastic (deformable) substrates have been developed for applications that require mechanical compliance (flexible and stretchable displays, tunable optics). Stretchable conductors usually show a steep increase in resistivity with stretch due to percolation effects. Current candidates for transparent electrodes have to balance transparency and sheet resistance.

Stretchable conductors used as electrodes for dielectric elastomer actuators have very demanding requirements. For example, the dielectric elastomer should remain conductive at large strains. Efforts to make stretchable, transparent solid-state electrodes have been confined to electronic conductors, with limited success. Compliant electrodes are commonly made of carbon grease; consequently, the transducers are greasy and opaque. Other conductive materials having higher transparency, for example, indium tin oxide (ITO. carbon nanotubes, silver nanowires and grapheme layers in or on the surface of elastomeric structures have been shown to combine transparency with stretchability. These solutions have one thing in common: the electrical resistivity strongly increases with stretch due to disruption of the conductive pathways in the stretchable conductor matrix—percolation in the case of nanotubes and nanowires and fracture in the case of graphene. Clearly, there is conflicting demand: increasing the amount of conducting particles decreases resistivity but at the same time transparency is also affected negatively due to the augmented amount of light scattering or absorbing particles. No solutions are available today for low sheet resistance at large strains paired with high transparency (for many industrial applications it is necessary to have transmittance >90%.

Our skin—a principal site to perceive the world—is a platform for stretchable, large-area sensors. This design in nature has inspired the development of "electronic skin". Existing designs of electronic skin rely on electronic conductors, which struggle to achieve high stretchability, along with attributes required in specific applications, such as biocompatibility in medical devices, and transparency in tunable optics. It has been challenging for these electronic conductors to meet various demands associated with sensor skins, such as high stretchability, biocompatibility, and transparency. By contrast, nature has chosen ionic conductors—nerves—to sense and distribute signals throughout our bodies.

SUMMARY

A new class of transparent and stretchable electrodes is described. The electrodes provide ultra-high transparency, liquid like behavior of resistivity during shape change and a wide variety of available charge carriers. This approach also allows the use of ionic conductors in high voltage circuits with frequencies up to tens of kilohertz.

In other aspects, transparent electrodes are shown as components of actuators with high speed electrostatic actuation. The stretchable electrodes combine perfect (or near perfect) transparency with low resistivity at large strains. The fully assembled actuator structure is highly transparent and yields transparent artificial muscles with large strain actuation (>100% area expansion) induced by high electric fields that are distributed by ionic conductors. In other aspects, the transparent electrodes are incorporated into a highly deformable, large-area system of sensors.

The transparent actuator uses layered electrolytes and dielectrics, sandwiching the dielectric elastomer between two sheets of an electrolyte elastomer, which in turn are connected outside the active area to metal conductors. The stretchable (elastic) conductors use ionic conductors to distribute the electric field on the elastomer membrane. The electrolyte elastomer conducts electricity by mobile ions and, at the interface with the metal, forms an electric double layer of large capacitance and small voltage drop. The electrolyte-dielectric elastomer is capable of high-speed, voltage-induced large deformation. This family of artificial muscles can be made as multilayers to carry large forces.

In one aspect, a transparent electrode includes an ionic electrode comprising an elastomer and an electrolyte solution dispersed throughout the elastomer to provide a transparent electrolyte; and a dielectric layer, wherein the ionic electrode is capacitively coupled with external signals by the dielectric layer.

In any of the embodiments, the transparent conductor further includes electrical connectors in electrical contact with the transparent electrolyte for connection to a voltage source.

In any of the embodiments, the electrode is used as stretchable wires/interconnects in circuits used in the field of stretchable electronics.

In another aspect, a transparent transducer includes a dielectric layer comprising an elastomer; a plurality of transparent electrolyte layers disposed across the dielectric layer, wherein the electrolyte layer comprises an elastomer and an electrolyte solution dispersed throughout the elastomer; and electrical connectors in electrical contact with the transparent electrolyte layers for connection to a voltage source.

In one or more embodiments, the boundary of the dielectric layer is constrained.

In one or more embodiments, the boundary of the dielectric layer is unconstrained.

In one or more embodiments, the transducer includes a plurality of dielectric layer, each dielectric layer having a plurality of transparent electrolyte layers disposed across the dielectric layers.

In any of the preceding embodiments, the dielectric layer and electrolyte layers are patterned.

In any of the preceding embodiments, the transducer further includes upper and lower layers that serve as vapor barriers.

In any of the preceding embodiments, the dielectric layer is disposed on a support in an extended (stretched) state.

In another aspect, a transparent sensor includes the transducer as described substantially herein; and connectors on the electrolyte layers for providing electrical connection to a capacitance meter.

In another aspect, a transparent loudspeaker includes a dielectric layer comprising an elastomer, wherein the dielectric layer is disposed on a support and the boundary of the dielectric layer is constrained; a pair of transparent electrolyte layers disposed across the dielectric layer, wherein the electrolyte layer comprises an elastomer and an electrolyte solution dispersed throughout the elastomer; and electrical connectors in electrical contact with the transparent electrolyte layers for receiving an audio signal from a voltage source.

In one or more embodiment, the loudspeaker operates at a frequency of up to 20 kHz. Higher frequencies are also possible; ultrasound applications could be interesting for underwater communication of submarines.

In any of the preceding embodiments, the electrolyte layer elastomer comprises a hydrogel or a lyogel. In certain embodiments, the lyogel can include an ionic liquid as a solvent. In other embodiments, the electrolyte layer can be ionic liquids alone, e.g., without elastomer, as they do not evaporate (have very low vapor pressure) and are of high viscosity so that they can remain in place.

In any of the preceding embodiments, the electrolyte solution is an aqueous salt solution, and for example, the aqueous salt solution includes a sodium chloride solution.

In any of the preceding embodiments, the aqueous salt solution has a salt concentration in the range of fully saturated to isotonic in physiological systems such as cells.

In any of the preceding embodiments, the aqueous salt solution has a minimum resistivity value of 0.02 Ohm-meter.

In any of the preceding embodiments, the transparent electrolyte layer has a transmissivity of greater than 95%.

In any of the preceding embodiments, the dielectric is transparent.

In any of the preceding embodiments, the dielectric is an elastomer.

In any of the preceding embodiments, the electrode is stretchable.

In certain aspects, the transparent actuator is incorporated into a transparent loudspeaker.

In other aspects, the laminate structure of layered electrolytes and dielectrics is incorporated into a transparent large-strain sensor.

The ability to incorporate transparent electrodes into electronic actuators provides adaptive optics where electromechanical transducers can be placed directly in the optical path (such as contact lenses with tunable focal length) or electronic devices with fully transparent elastomer actuators placed directly in front of the (touch) screen where they can provide localized vibrational haptic feedback or generate sound without impeding the viewing experience.

In other aspects, the invention provides sensor skins using ionic conductors. Such an "ionic skin" senses signals—with high stability and wide range—from a gentle touch of a finger to strains over 500%. Ionic conductors are abundant, providing rich opportunities to create a platform for highly stretchable, biocompatible and transparent sensory perception of diverse stimuli. The sensors have impressive sensing performance based on a simple and low-cost design that can be made fully transparent, highly stretchable, biocompatible and biodegradable. The sensors work at very low voltages (well below 1V if necessary), thereby broadening the possible application areas.

BRIEF DESCRIPTION OF THE DRAWING

The invention is described with reference to the following figures, which are presented for the purpose of illustration and are not intended to be limiting of the invention.

FIGS. 8A and 8B provide photographs of hydrogel capacitor (A) before and (B) after being stretched by 100% equibiaxial strain.

FIG. 8C is an exploded view of a strain sensor according to one or more embodiments.

DETAILED DESCRIPTION

A highly translucent electrode including a hydrogel electrolyte is described. The electrode is capable of operation at frequencies of greater than 10 Hz, and specifically at frequencies of greater than 1 kHz. In addition, the electrode can operate at applied voltages of greater than 0.1 V, and specifically at applied voltages of greater than 1V, without electrochemical breakdown of the electrolyte. In certain embodiments, voltages of up to 18000 V have been employed.

The ionic conductors can be used in electrical circuits that can (if necessary) carry large voltages and operate at high frequencies. Ionic conductors are very stretchable (if used in form of an elastomeric electrolyte), behave like liquids in terms of resistance when stretched, can be perfectly transparent and they can be elegantly biocompatible or biodegradable.

The class of ionic conductors compatible with large voltage, high frequency circuits is achieved using a dielectric in series with the ionic conductor. The interface of an ionic conductor with an electronic conductor also behaves like a capacitor (in series with the dielectric capacitor), but with very large capacitance compared to the second capacitor. This arrangement solves two problems: 1) The large capacitance of the ionic/electronic interface causes the voltage drop across this interface to always stay within the electrochemical window. 2) The overall capacitance of the circuit is dominated by the smaller capacitance (the dielectric). Thereby the RC time of the whole circuit is very small, resulting in high frequency capabilities of according devices. The device include at least one dielectric within the circuit. The dielectric can be flanked by either two ionic conductors or by one ionic conductor and on the other side an electronic conductor.

The transparent electrode includes an ionic layer that includes an elastomer and an electrolyte solution dispersed throughout the elastomer layer to provide a transparent electrolyte. The ionic layer is selected to be highly translucent to the selected range of visible light and to be elastomeric within the range required for the anticipated application. The ionic layer is capacitively coupled through a dielectric material. Capacitive coupling is typically achieved by placing a capacitor in series with signals to be coupled. In one or more embodiments, the dielectric layer forms a capacitor between the ionic layer and a second conductor in an electrical circuit.

Figure 1A:
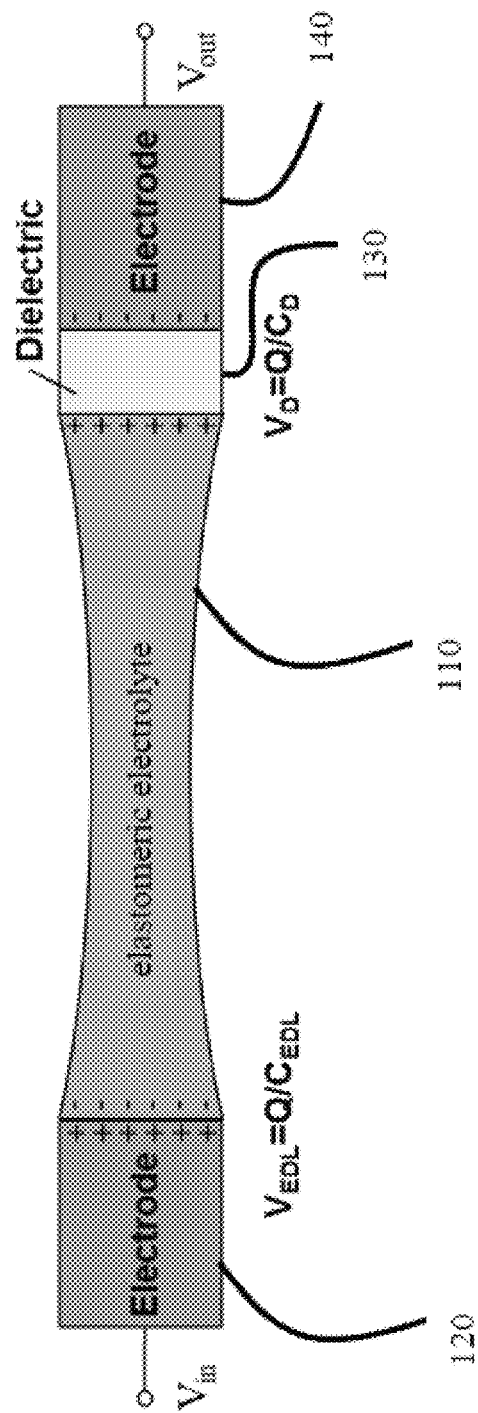
FIGS. 1A-1C are schematic illustrations of various aspects of using elastomeric electrolytes (ionic conductors) as parts of electronic circuits, showing (A) a cross sectional illustration of an electric circuit comprising electronic conductors, ionic conductors and a dielectric; (B) the interface between an electrode and an electrolyte that establishes an electric double layer; and (C) a plot of current vs. voltage at the interface showing an electrochemical stability window.
Figure 1B:
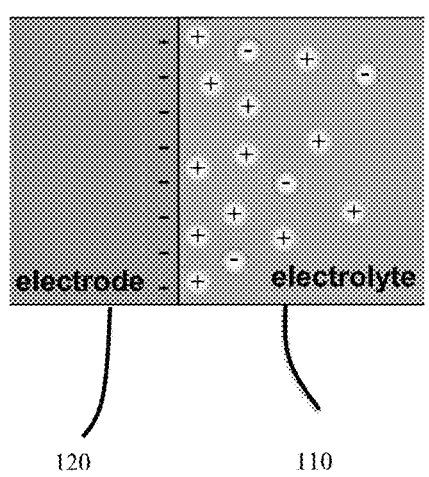
Figure 1C:
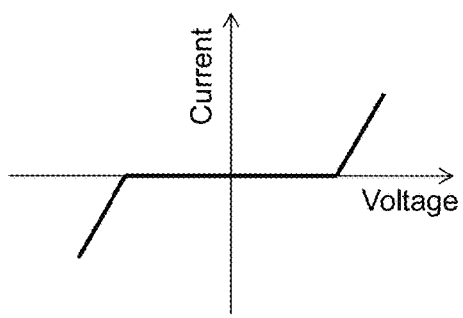

FIGS. 1A-1C illustrate various aspects of ionic conductors suitable for use in large voltage and high frequency circuits. FIG. 1A is a schematic illustration of a circuit including a transparent ionic conductor according to one or more embodiments. The transparent electrode includes a transparent elastomeric electrolyte 110 that is in electrical contact with an electronic conductor 120 and a dielectric 130. While shown here as an elastomeric layer in which the electrolyte liquid swells the polymer layer, it is also contemplated that the polymer can be other polymer types that are less flexible, or that the ionic electrode is an ionic liquid alone. Use of an ionic liquid without polymer support provides the greatest degree of flexibility to the ionic electrode layer. The dielectric can be connected in series with a second conductor 140 in an electric circuit. The second conductor can be an electronic or an ionic conductor. As shown in FIGS. 1A and 1B, when electronic (metal) and ionic (electrolyte) conductors are in contact in an electric circuit, e.g., at the interface between electronic conductor 120 and ionic conductor 110, electrons in the metallic wire and positive ions in the electrolyte form an electrical double layer at the interface. The electrons cannot move across the metal boundary and large electrostatic forces keep them in molecular distance from the oppositely charged ions, constituting an ultra-high capacitance on the order of $10^{-1}$ F/m$^2$ currently exploited in supercapacitors. As shown in FIG. 1C, the interface can be subjected to a voltage within a selected range (the electrochemical window) in which no electrochemical reaction occurs, e.g., no steady electric current flows across the interface; the electric double layer behaves like a capacitor. As further illustrated in FIG. 1A, the ionic conductor also forms a capacitor with the dielectric material 130. When two capacitors are connected in series, as is the case here, the amounts of charge on the two capacitors are the same, but the capacitance of the electric double layer is typically much larger than the capacitance of the dielectric, $C_{EDL} \gg C_D$. Much of the applied voltage drops across the dielectric, so that the voltage across the interface between electronic and ionic conductor can be small, well within the electrochemical window. The capacitance of the dielectric is typically small, therefore the device can be charged rapidly as the RC time of the whole circuit is governed by the smaller capacitance and the resistance of the electrolyte. When both the electrolyte and dielectric are elastomeric and transparent, the device is a stretchable and transparent solid.

Figure 6A:
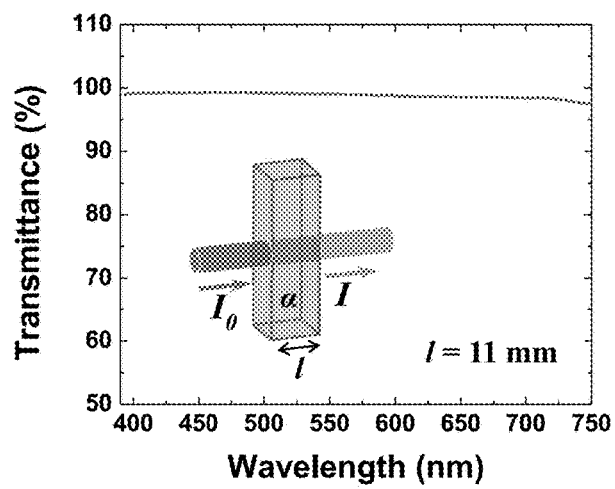
FIG. 6A is the transmittance spectra of a 11 mm thick hydrogel in the visible range demonstrating >99.99% transmittance of the transparent electrodes used in the actuator application.
Figure 6B:
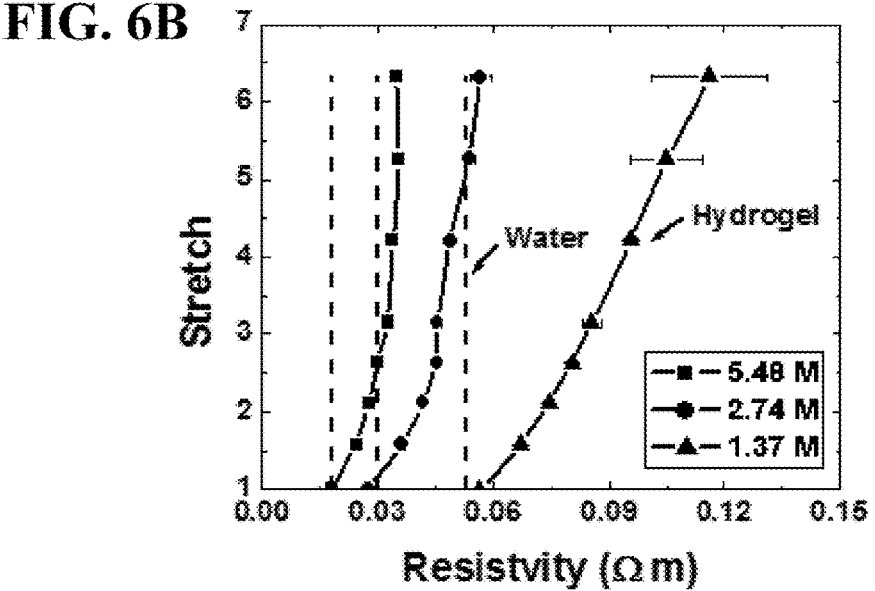
FIG. 6B is a plot of stretch vs. electrical resistivity for hydrogel with varying salt concentrations (solid lines) and salt water solutions of the same concentration (dashed lines).

The transparent electrolyte includes a transparent medium suitable for the transport of ions. In one or more embodiments, the ionically conductive medium is an aqueous salt solution. Any water soluble salt can be used; however, sodium chloride is a readily available, inexpensive source of ions. In other embodiments, non-aqueous medium can be used to form the ionically conductive medium. The conductive medium is supported by a polymer elastomeric network. An appropriate choice of polymer elastomeric network produces a fully transparent, elastomeric ionically conductive electrode. Salt concentration can vary over a wide range without affecting the function of the electrode. In FIG. 6B the resistivity of hydrogels is reported as a function of stretch using salt concentrations ranging from 1.4M to 5.5M. In FIG. 6B, dashed lines indicate resistivity of salt solutions at 5.48M, 2.74M and 1.37M, respectively. Corresponding curves indicate the change in resistivity with stretching. Salt concentrations near saturation show the lowest possible resistances (e.g., highest conductivities). Unlike other stretchable conductors that see a marked increase in electrical resistivity on stretching, the sale swollen hydrogel exhibited only a moderate increase in resistivity. For applications where biocompatibility of the hydrogel layer is important, salt concentration that are isotonic to cells can be used, especially in the actuator application.

In one or more embodiments the fully transparent, elastomeric ionically conductive electrode is a hydrogel. Hydrogels refer to materials that are able to take up and hold large volumes of water. Due to the large volume of water in the hydrogel network, the gels can exhibit high degrees of transparency. Hydrogels generally consists of a three-dimensional polymer network that is crosslinked chemically and/or physically. The chemical properties of hydrogels are typically determined by the polymer backbone, any functional side chains on the monomer units and the crosslinking agent. The physical properties, for example, mechanical strength and swelling ratio, are controlled typically by the crosslink density. Thus, hydrogels of extremely high transparency and suitable mechanical strength can be used. In one exemplary embodiment, polyacrylic acid, poly N-isopropylacrylamide (PNIPA), poly hydroxy ethyl methacrylate (PHEMA), poly ethylenene glycol (PEG), polyvinylalcohol (PVA), acrylamide is used as the base material for the hydrogel. Highly stretchable and tough hydrogels made from ionically crosslinked alginate, and covalently crosslinked polyacrylamide can also be used. In other instances, transparent, elastomeric and tough hydrogels from poly (ethylene glycol) can be made from PEG that has been covalently cross-linked through photopolymerization. A hydrogel containing slide-ring polymers, e.g., polymer networks threading polymer chains through polycyclic linkers, can be stretched to more than 10 times its initial length; a tetra-poly(ethylene glycol) gel has a strength of ~2.6 MPa. These gels deform elastically. A gel can be made tough and notch-insensitive by introducing energy-dissipating mechanisms. For example, a fracture energy of ~1,000 J-m$^{-2}$ is achieved with a double-network gel, in which two networks—one with short chains, and the other with long chains—are separately crosslinked by covalent bonds. Further details on the preparation of elastomeric hydrogels can be found in "Highly stretchable and tough hydrogels" Sun et al. *Nature* (489) 133 (Sep. 6, 2012), which is incorporated by reference. In one or more embodiments, hydrogel electrodes with a thickness in the range of 5 μm-1000 μm can be employed. Exemplary single layer devices can employ layers on the order of 100 μm. In multilayer devices, lower thicknesses will be beneficial, probably in the order of 10 μm or even less. If the requirement of the application is minimal sheet resistance of a transparent electrode, one can use higher thicknesses, as high as the geometrical constraints of the application will allow for.

One advantage of the electrolyte is that the resistivity is not adversely affected by stretching. Because the conductive framework of the hydrogel is an aqueous electrolyte solution, the electrolyte has the ability to flow within the hydrogel network. When the system is actuated and the electrolyte layers are stretched, the electrolyte solution is able to redistribute within the hydrogel network without disruption of the connectivity and conductivity of the electrolyte. The hydrogel electrodes feature transmittance near 100% at any deformation state and an electrical resistivity that is competitive at small strains and superior at large strains to any existing solution of transparent stretchable electrodes. In one or more embodiments, the transmissivity is greater than 95%, or greater than 99%, or greater than 99.9%.

Any material having a sufficiently high dielectric strength may be used as the dielectric layer. The insulating properties of the layer play a role in the device performance, especially in the actuator application. While not required to be elastomeric or transparent in order to be used in a high frequency, high voltage circuit, the use of such transparent, elastomeric materials provides a transparent and flexible electrode system. Exemplary elastomer includes a silicone rubber, an acrylonitrile-butadiene rubber (NBR), a hydrogenated acrylonitrile-butadiene rubber (H-NBR), an ethylene-propylene-diene rubber (EPDM), an acrylic rubber, a urethane rubber, an epichlorohydrin rubber, a chlorosulfonated polyethylene, and a chlorinated polyethylene. The common material in the actuator application is VHB 4910. Exemplary transparent dielectrics include PDMS, also acrylic rubbers. Additional suitable dielectric elastomers are described in Journal of Polymer Science, Part B: Polymer Physics, 2013, 51, 197-206, which is incorporated in its entirety by reference. Suitable thickness can depend on the intended application. In a general circuit, there are no special requirements for the thickness. The higher the thickness, the lower the capacity, and the higher the maximum frequency. In the actuator application, typical thicknesses range from 10 μm to 1 mm.

In other embodiments where the high flexibility and stretchability of elastomers is not required, other dielectric materials can be used. For example, piezoelectric polymers such as polyvinylidene difluoride (PVDF). This design would not be stretchable, but has advantages such as lower required voltages and linear dependence on driving voltage.

The electrolyte is electrically connected to electronically conducting electrodes. The electrodes provide electrical contact to external voltage sources used to actuate the device or as an electronic signal. Conventional conductive materials, such as metals, can be used for the electrodes. Exemplary electrodes include gold, copper, silver, or any other metal. Also possible are electronic conductors based on carbon, such as carbon grease, carbon particle impregnated elastomers, carbon fibers, graphene etc. These electrodes can be placed outside the region that needs to be transparent, conductive and stretchable at the same time. There are no limitations with respect to thickness of the electronically conducting electrode; however, the overlapping area of electronic conductor and ionic conductor will prescribe the interface capacitance of the electric double layer. This will influence the voltage drop across the interface and thereby the electrochemical stability. Geometries with high surface area (such as a carbon mesh or porous carbon) can be used to increase this overlapping area when available contact space is limited due to design considerations.

The transparent, elastomeric ionic electrode can be included in a variety of devices, giving rise to a variety of circuit arrangements. For example, a pair of elastomeric electrolyte layers can be used to sandwich a central elastomeric dielectric to form an elastomeric actuator. In other embodiments, alternative layers of elastomeric electrolyte and dielectric can be stacked together. Such multilayer configurations are suitable for use in industrial applications such as actuators in speakers and microphones. Multilayer configurations can achieve high actuator performance with much lower voltages than single layers of the same total thickness. Lower voltages will reduce the size and cost of the driving electronics and also increase the electrical safety of the device. Especially in the context of multilayer configurations the high transparency of the conductor provides heretofore unattainable performance. The high transparency of each layer provides a final multilayer device with excellent transparency, despite multiplicative effect of the multiple layers in reducing transparency.

In other embodiments, the electrodes can also be used as stretchable, transparent wires (interconnects). In one or more embodiments, cylindrical or rectangular cross sections of the wire can be used. In certain embodiments, the wire interconnect includes a central cylindrical region containing an elastomeric electrolyte, surrounded by a cylinder of dielectric, and then another layer of elastomeric electrolyte. Electronic connections can be located at the top and/or bottom of the cylinder.

Other geometries and arrangement of ionically conducting hydrogel and dielectric are contemplated; it depends a lot on the planned applications.

Figure 2A:
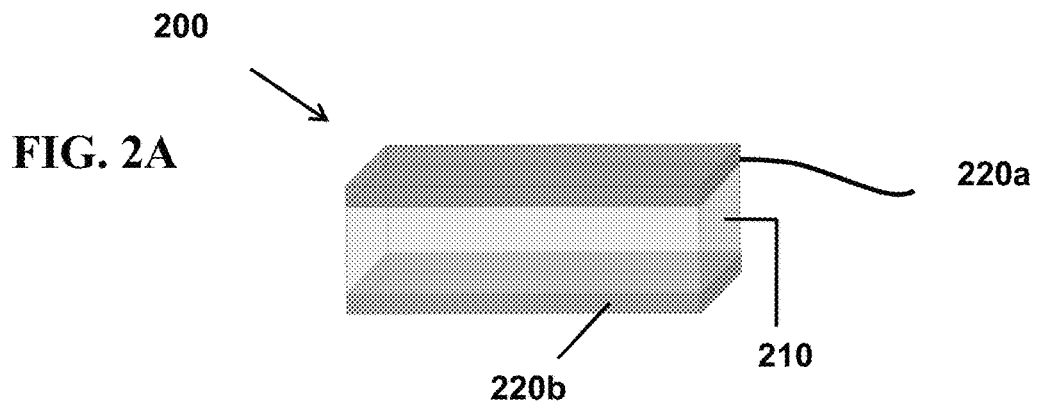
FIGS. 2A-2B are schematic illustrations of activation in a dielectric elastomer (A) as rest and (B) under applied voltage.
Figure 2B:
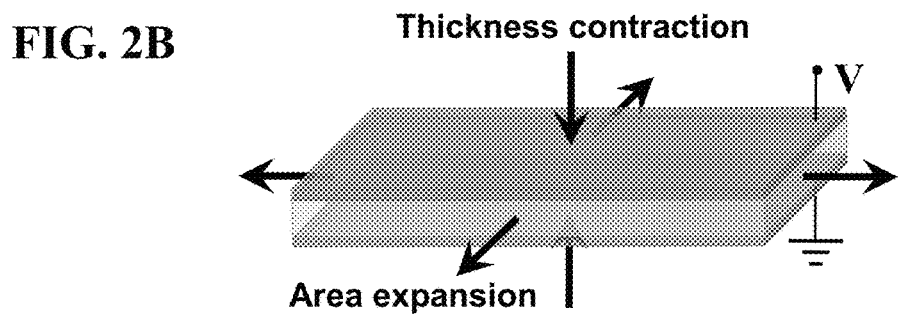

FIG. 2A is a schematic illustration of a stretchable ionic electrode 200 according one or more embodiments of the invention, which can be used in a transparent electronic actuator, wire interconnect or sensor for example. Dielectric elastomeric actuators are an elastomeric polymer sheet 210 sandwiched between two compliant electrodes 220a and 220b. In contrast to conventional electronic electrical conductors used in an electronic actuator, the transparent actuator uses ionic conductors as electrodes that flank the central dielectric elastomer. As shown in FIGS. 2A and 2B, an actuator 200 includes a dielectric film 210 and hydrogel electrolyte layers 220a and 220b. FIG. 2B illustrates this mode of actuation for a transparent actuator including ionic electrodes. Applying a voltage between the electrodes creates a compressive electrostatic force which squeezes the film and, under free boundary conditions, causes the film's area to expand as indicated by the arrow in FIG. 2B.

In ionic conductors, electrical current is accomplished by moving ions through the medium; materials that rely on ions for current transport are typically referred to as "electrolytes". Thus, the transparent actuators rely on the use of transparent ionic conductors, or transparent electrolytes, as electrodes. The transparent electrolyte includes a transparent medium suitable for the transport of ions. The materials and material combinations discussed above for the transparent ionic electrode can be used to form a transparent actuator.

Figure 3A:
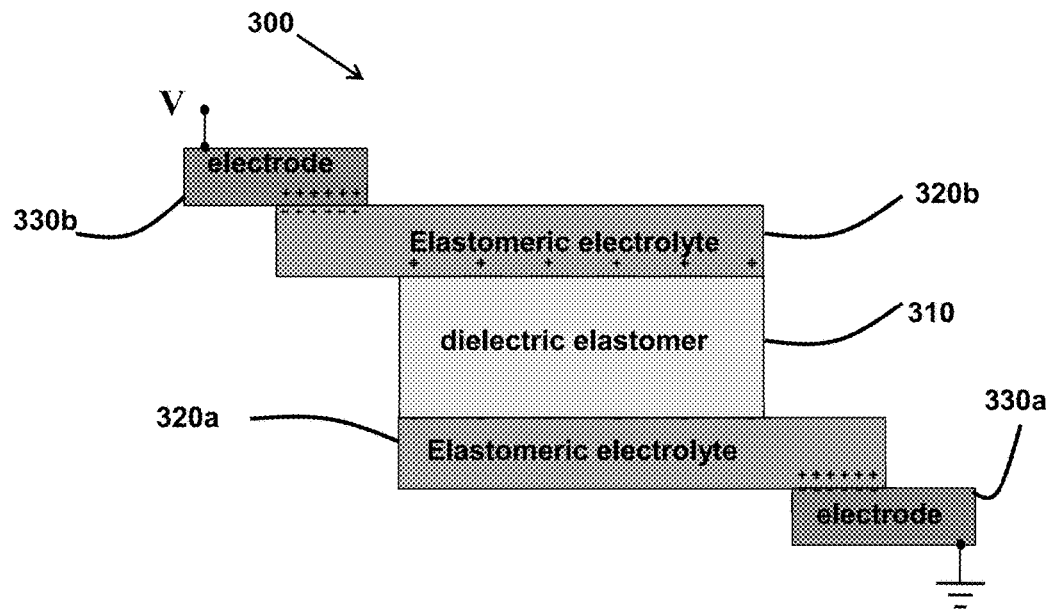
FIG. 3A is a schematic illustration of an actuator including an elastomeric ionic electrode according to one or more embodiments and FIG. 3B is an equivalent circuit.

FIG. 3A is a cross-sectional view of an electromechanical actuator 300 according to one or more embodiments. The actuator includes a dielectric elastomer 310 flanked on opposing sides by electrolyte layers 320a, 320b. The electronic contact electrodes 330a and 330b are connected to a power source (not shown). The electrolyte layers are electrically connected to electrodes 330a and 330b at a perimeter edge of the electrolyte layer. The electrodes provide electrical contact to external voltage sources used to actuate the device. The electrodes 330a and 330b are typically electronically conductive materials such as metals or other materials with high electronic conductivity. It is not necessary to use high transparency materials for the electronic conductor as the electrodes do not obscure at least a portion of the transparent window defined by the elastomeric electrolyte and elastomeric stacking; conventional electrodes can be used. Exemplary electrodes include gold, copper, silver, or any other metal. Also possible are electronic conductors based on carbon, such as carbon grease, carbon particle impregnated elastomers, carbon fibers, graphene etc. When switching from the OFF state to the ON state, voltage is applied between the pair of electrodes 330a and 330b.

Figure 3B:
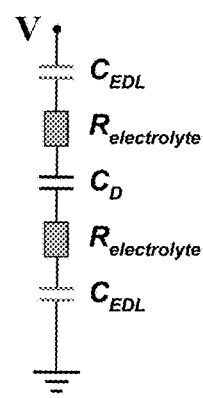

Effectively, the device may be represented as an equivalent circuit as shown in FIG. 3B. Note that in this device three capacitors are connected in series (compared to the two capacitors for the device of FIG. 1A). However, even the more complex system here includes capacitive coupling between an electrolyte layers (320a, 320b) with a dielectric layer (310). Because the electrolyte behaves as a capacitor in series with the dielectric, the charge across the dielectric and the double layer formed at the metal/electrolyte interface is identical: $Q_{interface}=Q_{dielectric}$ and the voltage drop across the interface is small to prevent electrochemical decomposition.

In one embodiment, the actuator includes highly elastic and stretchable thin films that allows it to function as a transducer. A transducer is an electromechanical transducer can convert electrical energy into mechanical energy and vice versa. In one or more embodiments, the transducer can function as an actuator and/or a sensor. Multilayer structures as described herein can be useful for sensor and for actuator applications.

In one embodiment, the actuator includes highly elastic and stretchable thin films of hydrogel swollen with a transparent ionically conducting liquid ($H_2O$+NaCl) sandwiching an acrylic dielectric elastomer membrane to form capacitive electromechanical transducers. The hydrogel thickness in one exemplary embodiment is 100 μm; however, the thickness can vary depending upon the particular application. For multilayer actuators, electrode thickness can be reduced to the order of 10 μm or even lower depending on manufacturing capabilities. A metal (alligator clips) or copper electrodes were used as the electronic conductor.

In certain embodiments, a grid of carbon fibers can be used as an electrode. Porous carbon structures, such as those used in supercapacitors, can also be used. Carbon is chemically very stable and a fiber structure has a high surface area for a given size of electrode. High surface area will increase the size of the electric double layer and thus the capacitance of this interface, which in turn will result in a lower voltage drop across this interface (and thereby prevent electrochemical effects at the interface).

In certain embodiments, the electrolyte has sufficient mechanical integrity to be formed into sheets that can cover and optionally extend over the edge of the dielectric elastomer. While sheet extension is not required, it has the advantage of increasing the area of transparency. For example, the electrolyte can be electrically connected to electrodes at an edge portion that extends beyond the dielectric elastomer region. Thus, the entire dielectric elastomer surface area is transparent and not visually impeded by the electrode connections.

In an actuator according to one or more embodiments, when the applied voltage between the ionic electrodes is increased, the electrolyte distributes the electric field on the dielectric elastomer membrane and an electrostatic attraction between the electrodes increases. Therefore, the dielectric film sandwiched between the electrolyte is compressed in a thickness direction and the thickness of the dielectric film decreases. When the film thickness decreases, the dielectric film proportionally extends in a horizontal direction with respect to the electrode surfaces. To reverse the action, the applied voltage between the electrodes is reduced, and the electrostatic attraction between the electrodes decreases. Therefore, the compressive force on the dielectric film in the thickness direction is reduced, and the film thickness increases due to an elastic restorative force of the dielectric film. When the film thickness increases, the dielectric film proportionally contracts in the horizontal direction with respect to the electrode surfaces. In this way, the actuator drives drive target members by extension and contraction of the dielectric film in response to the magnitude of the applied voltage.

In certain embodiments, the transparent electrode is constrained to a pre-selected geometry. For example, the size of the electrode is set by fixing the electrode on a rigid frame. In certain embodiments, the transparent electrode is stretched before securing to the frame. This arrangement can be used in loudspeaker arrangements. Upon application of a voltage between the electrodes, compressive stress builds up in the membrane and the electrode shape expands in area and is deflected. In some embodiments, the (prestretched) dielectric elastomer layer is glued to the rigid frame and the hydrogel layers cover only the central area of this membrane In certain embodiments, the transparent electrode is not constrained and the elastomeric layers are allowed to expand and contract as forces (e.g., electrostatic, strain or pressure) are applied to the electrode.

Previously, it was thought that electrolytes could not be used for actuation of electromechanical device because of the potential for electrochemical instability at the high voltages used for actuation. Without being bound by any particular mode or theory of operation; however, it is theorized that the huge capacity of the electrical double layer formed at the interface between ionic conductor and electronic conductor (external electronics) allows for placing the potential drop at this interface into the electrochemical window in order to suppress chemical reactions.

It had also been previously believed that electrolytes were unsuitable for use in a dielectric elastomer type actuator because ion mobility was too slow for actuation at speed necessary for most applications. It has been surprisingly shown that the elastomeric electrolyte-dielectric elastomer laminates exhibit electrically induced strains >100% and (despite being based on ionic conductors) high speed actuation up to 20 kHz. The high strains and high speed actuation permit the ionic conductor actuator to be used to create sound.

The hydrogel electrodes feature transmittance near 100% at any deformation state and an electrical resistivity that is competitive at small strains and superior at large strains to any existing solution of transparent stretchable electrodes. These unique electrical properties are further showcased with a large strain, transparent capacitive strain sensor. This new class of transparent electrodes for dielectric elastomer actuators can be optimized for patternable multilayer configurations and industrial manufacturing requirements. For example, the mechanical properties of the hydrogel can be altered, such as by varying crosslink density. Laser cutters can be used to cut films of hydrogels in special and sophisticated shapes. Furthermore the fact that hydrogel are liquid before they are crosslinked makes them suitable for (injection) molding techniques, maybe even to be used in 3 d printers, etc.

The diversity of ionic conductors creates a large pool of candidates that can be selected for a specific application. The transparent electrode is described above with reference to hydrogels as the transparent elastomer used in the ionic electrolyte; however it is contemplated that other ionic medium can be used. Hydrogel based devices can be appropriate in humid environments or locations with high moisture content, such as the human body. The hydrogel is advantageous for biomedical applications that require biocompatibility or biodegradability. However, evaporation of water from a hydrogel may affect the ability of using the electrode for long periods of exposure or in dry environments.

(a) Reducing Evaporation Using Non-Volatile Liquids

In some embodiments, the transparent electrode can be prepared using non-volatile liquids. Non-volatile liquids that are capable of swelling a polymer network provide transparent elastomeric electrolytes that are more durable and less susceptible to performance impairment due to evaporation.

In certain embodiments, ionic conductors can be used in the liquid form (with appropriate viscosity to avoid running around). From a mechanical point of view, the liquid form has zero mechanical stiffness, thereby constraining area expansion of a dielectric elastomer actuator the least. The ionic conductor in a liquid form could also be housed in elastomeric channels/compartments/containers; it is not required that the liquid ionic conductor swell the elastomeric support.

In some applications, it is advantageous to have the ionic conductor in an elastomeric form, in order to keep it in place and prevent it from running around. But in general this is not required for the operation of the device.

One exemplary non-volatile liquid is ionic liquids. Ionic liquids are electrolytes. Ionic liquids can be used alone to swell the polymer electrolyte or they can be used in combination with a solvent that swells the polymer network. A large number of ionic liquids exists, and may be selected to suit specific applications. Furthermore, ionic liquids can be used as solvents to form ion gels, which are stretchable, transparent, ionic conductors. Ionic liquids can be used to swell a polymer network and thereby create a material with similar properties to the hydrogels. The ionic liquid gel does not degrade in dry environments. An ionic liquid (IL) is a salt in the liquid state. While ordinary liquids are predominantly made of neutral molecules, ionic liquids are largely made of ions. Thus the ionic liquids serve as a natural ionically conductive medium that both swells the polymer network and provides ionic conductivity. Additional salts or solvents can be added. Exemplary, non-limiting list of ionic liquids includes nitrogen cation moiety having a nitrogen cation selected from the group including but not limited to an imidazolium, ammonium, pyridinium, piperidinium and pyrrolidinium nitrogen cation moieties. Variations using other known ionic liquids, including for example, ammonium, pyridinium, piperidinium and pyrrolidinium nitrogen cation moieties, as well as phosphonium and sulfonium cation moieties can also be used.

(b) Reducing Evaporative Loss Using Encapsulation

In other embodiments, vapor loss can be reduced by encapsulation of the transparent electrode with additional layers of elastomers. Suitable materials such as parylene (especially type C) or nitrile butadiene rubber (NBR) to prevent (or slow down) evaporation can be used.

(c) Reducing Evaporation Using Deliquescent Materials

Deliquescent materials are substances (mostly salts) that have a strong affinity for moisture and will absorb relatively large amounts of water from the atmosphere if exposed to it, forming a liquid solution. Deliquescent salts include calcium chloride, magnesium chloride, zinc chloride, potassium carbonate, potassium phosphate, carnallite, ferric ammonium citrate, potassium hydroxide, and sodium hydroxide. Using deliquescent salts such as calcium chloride or lithium chloride helps to retain moisture in a hydrogel because the salts themselves tend to retain environmental moisture.

In one or more embodiments, the sodium chloride salt described in the preceding transparent electrodes is replaced by a deliquescent salt such as calcium chloride or lithium chloride. By replacing NaCl as the salt in the hydrogel, properties of the resulting material with respect to evaporation change significantly. LiCl based systems will not evaporate even in environments with low relative humidity. For example, lithium chloride forms a self-solution when exposed to air. The equilibrium LiCl concentration in the resulting solution is directly related to the relative humidity of the air.

d) Reducing Evaporation Using Humectants

A humectant is any one of a group of hygroscopic substances used to keep things moist. A humectant attracts and retains the moisture in the air nearby via absorption, drawing the water vapor into and/or beneath the surface. The humectant property is associated with the compound's ability to form hydrogen bonds with molecules of water. This property can be used in the transparent electrodes described herein to assist in the adsorption and retention of water in the electrode. Exemplary humectants include molecules with several hydrophilic groups, most often hydroxyl groups; however, amines and carboxyl groups, sometimes esterified, can be encountered as well. Exemplary humectants include propylene glycol, hexylene glycol, butylene glycol, glyceryl triacetate, vinyl alcohol, neoagarobiose, sugar alcohols/sugar polyols such as glycerol, glycerin, sorbitol, xylitol, maltitol, polymeric polyols, quillaia, urea, aloe vera gel, alpha hydroxy acids (e.g., lactic acid) and honey.

By replacing parts or the entirety of the water in the hydrogel with humectant, such as glycerol (or related materials of hygroscopic nature from the family of humectants) the evaporation process is slowed down significantly. Glycerol is elegantly biocompatible.

One or more of the approaches described herein can be used, alone or in combination to reduce the evaporation rate of ionic solution used in the preparation of the elastomeric electrolyte used herein in the preparation of a transparent electrode.

Applications

I. Actuator Mode, Localized Haptic Feedback on Touch Screens

The superior transparency of our actuators will allow for a placement in front of (stretchable) (touch) screens. The extremely high transparency enables the use of multilayer configurations with unmatched performance compared to existing techniques (for example placing carbon nanotubes on the surface of dielectrics; at the required very high levels of transparency hydrogels show a much higher conductivity in comparison). A patterned structure of our actuators on the screen will allow for localized haptic feedback for electronic devices such as smart phones.

In one or more embodiments, the actuators can be configured in an array (to provide a 'touch pad' in which responses are geographically located). This could be made into a fully transparent, deformable layer that can be put in front of a screen. With one single array design this can be used to detect location and amount of finger pressure (human input device), but also function as an actuator array, which can provide localized haptic feedback or generate sound.

II. Transparent Loudspeaker

High frequency capability of these actuators is demonstrated by using them as fully transparent membrane loudspeakers with a measured frequency response that fully covers the human hearing range up to 20 kHz. The device can be operated at high enough frequencies to create sound and the ability to reproduce sound across the entire spectrum of human hearing from 20 Hz to 20 kHz has been demonstrated. Operation at higher frequencies such as from 20 kHz to up to several gigahertz (GHz), e.g., 20 Hz to 20 kHz, 20 kHz to 1 MHz, 1 MHz to 100 MHz, 100 MHz to 1 GHz and/or 1 GHz to 10 GHz.

As in the actuator mode the transparent loudspeaker can be placed in front of the screen of smartphones to use a large area for superior sound emission. Again, the very high transparency will allow for multilayer systems that outperform alternative solutions. Similarly, our transparent loudspeakers can be placed in front of larger scale screens such as LCD/LED flat screens or computer monitors. The larger available area would provide a base for high quality and very directed sound. At the same time our technology could reduce the weight of the screens. Other possible application options of our transparent loudspeakers include the placement on windows to turn them into high fidelity loudspeakers with zero visual impact. Placed on shop windows the transparent loudspeakers according to one or more embodiments could advertise products with immersive sound effects. Transparent loudspeakers would be generally interesting for fashionable designer loudspeakers. Most probably transparent loudspeaker would make a lot of impact in any living room.

In one or more embodiments, the loudspeaker to work even above 20 kHz, without any change in design. This could allow for applications in the field of ultrasound.

For the actuator/loudspeaker application the dielectric elastomer can be replaced with piezoelectric polymers such as polyvinylidene difluoride (PVDF). This design would not be stretchable, but has advantages such as lower required voltages and linear dependence on driving voltage (this removes the requirement of having a DC bias as in the loudspeaker application based on dielectric elastomers).

III. Transparent Sensors

Conventional, piezoresistive metal-foil strain gauges have very limited measurable strain range (under 5%), relatively stiff substrates, and opaque metallic films. They are practically not suitable for use in the low-stiffness and high-strain environments that characterize many medical applications and soft robotics systems. Moreover, since they are not transparent, most of the information about surface morphology and optical property change during deformation will be shaded by their opaque metallic films. Recently, many efforts to address these problems have focused on carbon nanotube or silver nanowire based sensors.

The basic design of ionic sensors is surprisingly robust, simple and low-cost, whereas the functionality and performance surpass many parallel approaches with much higher complexity. The available palette of materials that can be used includes many candidates, which are transparent and biocompatible. The sensors incorporating an elastomeric electrolyte can be designed to respond to changes in pressure and strain, as well as other stimuli, such as temperature, humidity and changes in pH (for example where and environmentally responsive hydrogel is used in the elastomeric electrolyte. The mechanical compliance of the sensors allows for application on "complicated" and dynamic surfaces. For example, a transparent, stretchable touchpad senses the location of touch in addition to delivering information about the exerted pressure. This characteristic could be useful for human machine interfaces in front of screens. The near to perfect transparency will not impede the viewing experience and the transparent keypad can detect the location and pressure of touch. Current touch screen solutions only detect the xy-location, but not the exerted pressure.

Since hydrogel electrolyte shows best transmittances of visible light, and has more stable and predictable resistance under stretched conditions compared to other stretchable electrodes, strain sensors based on hydrogel electrodes (and other elastomeric electrolytes as described herein) could offer superior performance. An electromechanical transducer sandwiches a dielectric elastomer between two layers of hydrogel (elastic, solid state) swollen with salt water. This stretchable capacitor changes capacitance when stretched, which can be used to measure deformation, which is the sensor mode. Such sensors could be placed on the human body or on soft machines to monitor movements or create feedback loops for control systems. The elastomeric electrolyte that houses the ionic conductor takes a solid form, yet behaves like a liquid under deformation with respect to resistivity. The solid form of the electrolyte layer eliminates the need for containers as required in the case of liquid conductors, thereby decreasing bulk and complexity of the sensors. Ionic sensors can be made softer than tissue, enabling the ionic skin to sense large deformation without distorting strain field, rendering the ionic skin "mechanically invisible". The softness of sensors is advantageous when used for soft organs like heart and brain, so that the sensors do not perturb their functions.

Many hydrogels that are currently used in biomedical applications and are biocompatible can be adapted for use in ionic sensors. In this design, both the ionic conductor and dielectric are transparent. The transparency of the ionic skin enables the monitoring of the surface underneath during deformation. If required by design constraints, ionic conductors are also perfectly suitable to be employed in resistive type strain sensors.

In certain embodiments, the ionic sensor includes a stretchable (e.g., elastomeric) dielectric sandwiched between two stretchable (e.g., elastomeric) ionic conductors, connected through metallic electrodes to an external electronic system. When external forces stretch the ionic skin, the dielectric expands area, reduces thickness, and increases capacitance. Through this change in capacitance, the ionic skin senses the stretch. Even though the resistivity of ionic conductors is much higher than that of a typical metallic conductor, the capacitance is low, resulting in fast electrical response. The electrodes connect with the ionic conductors in regions outside the active area of the device, so that the device is highly stretchable and transparent.

In one or more embodiments, the sensor is connected to a capacitance meter. In other embodiments, it is also possible to superimpose a voltage from a voltage source with the measurement signal of a capacitance meter. This would give an actuator that can sense the deformation state at the same time.

In one or more embodiments, a plurality of pressure or strain sensors can be incorporated into an area, each sensor independently responsive to a change in pressure or strain. The plurality of sensors can be associated with specific geographical or areal locations, so that information relating to strain or pressure at a specific location can be obtained.

Such area specific sensing can be used to produce transparent ionic touchpads. The touchpad senses the levels of pressure (or strain) and as well as the location of the output source.

Other sensing application as artificial skin with other human—and 'superhuman'—characteristics, such as the ability to sense moisture, temperature, light and even chemical and biological species are contemplated. Ionic skin provides opportunities for designers of soft machines and wearable electronics. The sensors can also be used for voltage sensing.

IV. Flexible Electronic Interconnects

Figure 10:
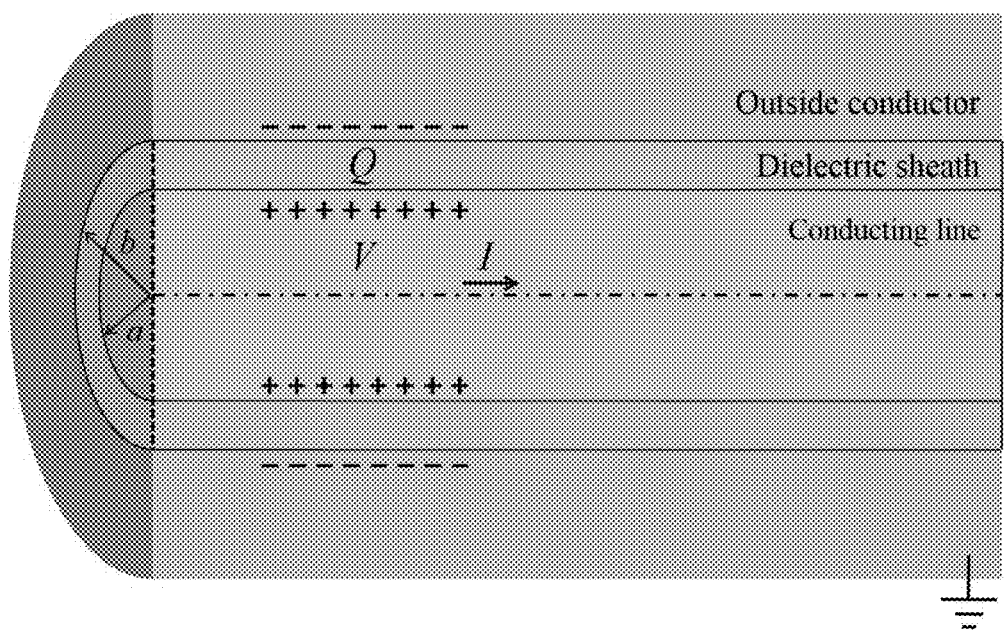
FIG. 10 is a schematic illustration of a model ionic conducting line according to one or more embodiments.

In other embodiments, the electrodes can also be used as stretchable, transparent wires (interconnects). In the actuator and loudspeaker, we connect the active regions of the devices to the copper electrodes using thin lines of ionic conductors. In one embodiment, an ionic conducting line is inside a dielectric sheath, which is surrounded by another conductor. This design demonstrates that ionic conductors can be used as high-speed, stretchable and transparent interconnects. Stretchable, transparent, ionic conductors can act as "artificial nerves". FIG. 10 is a schematic illustration of a model ionic conducting line according to one or more embodiments. The line propagates an electrical signal along arrow I along the length of the interconnect. FIG. 10 indicates the charge separation around the dielectric sheath. The outside conductor is grounded.

V. Tunable Optics

The transparency and the ability to change shape when voltage is applied suggest the use of our system in tunable optics, such as lenses with tunable focal length or aperture. Potential fields of use are lenses for smart phone cameras.

In all of the above-noted applications, one or more of the inventive features discussed above relating to the composition, design and use of the ionic electrode can be used, either alone or in any combination.

Example 1. Transparent Ionic Gel Conductor Preparation

The ionic gel conductors were prepared by dissolving Acrylamide (AAm monomer) powder and NaCl into the deionized water. Molar concentration of AAm was fixed as 2.2 M throughout the entire experiments, and molar concentration of NaCl was varied from 1.37 to 5.48 M. N,Nm-ethylenebisacrylamide (MBAA) 0.06 wt.-% and Ammonium persulfate (AP) 0.17 wt.-% with respect to the weight of AAm monomer were added as a cross-linker for AAm and a photo initiator, respectively. After degassing in vacuum chamber, N,N,N',N'-tetramethylethylenediamine (TEMED) 0.25 wt.-% with respect to the weight of AAm monomer were lastly added as the accelerator. The solutions were poured into a glass mold which has 100.0×100.0×0.1 mm$^3$ size vacancy and covered with 3 mm thick transparent glass plate. The gels were cured by the ultraviolet light cross-linker (UVC 500, Hoefer) for 20 min with 8 W power and 254 nm wavelength. The gels were then cut into the designed shape by using laser cutting system (VersaLaser VLS3.50, Universal Laser Systems) with 50 W power and 14 cm/sec beam speed. Before stacking hydrogel on top of VHB, the surfaces of the hydrogels were dried with N2 gas for 1 minute to improve the adhesion between gel and VHB by removing water from the gel surfaces.

Example 2. Transparent Artificial Muscle with Ionic Conductors

The effect of electrochemical reactivity at the interface between electrolyte and electrode on the performance of the device is considered. When an electric potential is externally applied between the electrodes in FIG. 3A, electrons in the metallic wire and positive ions in the gel form an electrical double layer at the electrode-electrolyte interface. If the voltage drop at the interface between electrolyte and electrode is larger than the electrochemical potential window between electrode material and ions, either oxidation or reduction will happen. Since the device may lose its functionality in cases of gas formation and insulation layer deposition, electrochemical reactions should be avoided or minimized. One way to avoid electrochemical reaction is increasing the area of interface between electrolyte and electrode. Before the onset of electrochemical reaction, because charge carriers cannot cross the interface under an applied voltage, the behavior of the interface is analogous to that of a capacitor. Consequently, the electrolyte behaves as a capacitor in series with a resistor. Effectively, the laminate may be represented as an equivalent circuit in FIG. 3B. Because the electrolyte behaves as a capacitor in series with the dielectric, the charge across the dielectric and the double layer formed at the metal/electrolyte interface is identical: $Q_{interface}=Q_{dielectric}$. Thus it can be shown that the ratio of voltage drop is related to the capacitance ratio:

$$\Phi_{dielectric}/\Phi_{interface}=C_{interface}/C_{dielectric}.$$

At the interface, the capacitance per unit area, ci, is on the order of $10^{-1}$ F/, which is much larger than the capacitance per unit area of the dielectric is $c_d=10^{-8}$ F/m$^2$. Using representative values, the maximum voltage drop across the interface is estimated to be $\Phi_{interface}$~0.1–1 V. For comparison, the electrochemical potential window for ion gels is about 4V. Since the voltage drop across the interface is inversely related to the interfacial area, the voltage drop across the interface could be smaller by increasing the interfacial area. This may be achieved, for instance, by using a grid of carbon fibers as an electrode.

A further issue is the comparatively slower speed of ionic conduction compared to electronic conductors. However, ionic conduction is fast enough to generate sounds up to extreme frequency, 20K Hz (see Example 4, and FIG. 7). For the series connection of capacitor and resistor like FIG. 3B, the net capacitance of the laminate C is given by $$\frac{1}{C} = \frac{2}{C_{interface}} + \frac{1}{C_{dielectric}}$$

and the net resistance for the laminate is:

$$R=2R_{metal}+2R_{electrolyte}$$

Since the net capacitance is dominated by the contribution of the dielectric, $C_{dielectric} \ll C_{interface}$, and the net resistance is dominated by the contribution of the electrolyte, $R_{metal} \ll R_{electrolyte}$, the RC time constant of the laminate, τ, is equal to the product of the net resistance R and the net capacitance C:

$$\tau=RC$$

Consequently, the RC time constant for the laminate under equilbiaxial stretching may be written as:

$$\tau = \frac{2\varepsilon_{dielectric} A_{dielectric} \rho_{electrolyte}}{H_{dielectric} H_{electrolyte}} \lambda^6$$

where dielectric $\varepsilon_{dielectric}$ is the permittivity of the dielectric, and $\rho_{electrolyte}$ is the resistivity for the electrolyte. τ typically ranges from $10^{-9}$ to $10^{-4}$ s, for a sample size $A_{dielectric}$=400 mm$^2$ and 1<λ<6.

Example 3. Transparent Artificial Heart

Figure 4A:
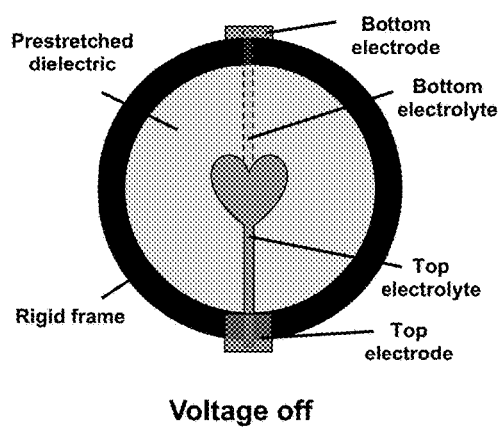
FIGS. 4A-4B are schematic illustrations of a transparent artificial heart prepared by sandwiching a dielectric elastomer between two sheets of elastomeric electrolyte as viewed in the (A) relaxed and (B) actuated states.
Figure 4B:
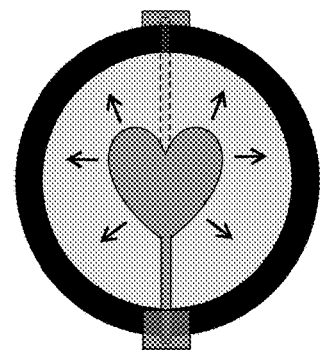
Figure 4C:
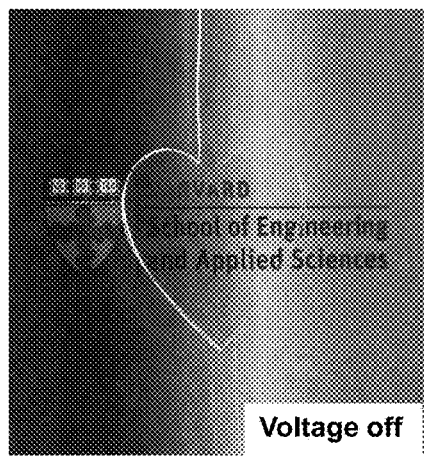
FIGS. 4C and 4D are images of the transparent artificial heart shown in FIGS. 4A and 4B, respectively, demonstrating the transparency of the device.
Figure 4D:
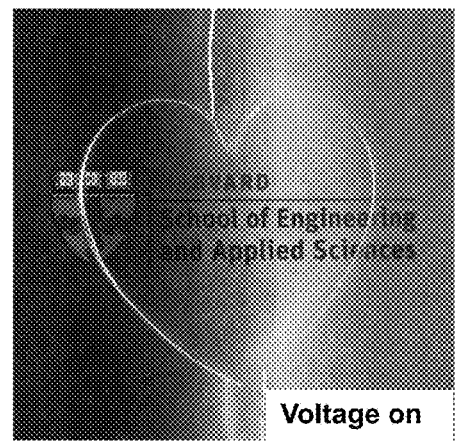

In FIGS. 4A and 4B, a transparent artificial heart was demonstrated by sandwiching the dielectric elastomer between two sheets of electrolytes. 3 layers of VHB 4910 tape (3M) were stacked together and pre-stretched with stiff acrylic frames. Upon application of a voltage between the electrodes, compressive stress builds up in the membrane and the heart shape expands in area, e.g., the heart "beats".

Figure 5A:
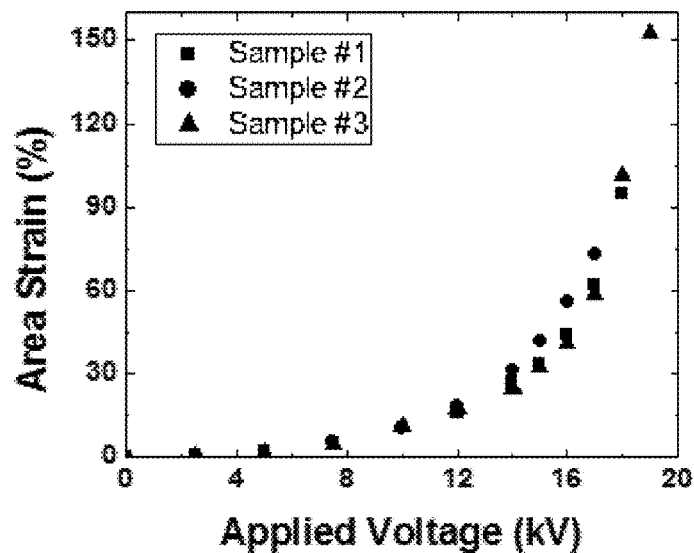
FIG. 5A is a plot of % area strain v. applied voltage showing the actuation of a circular DE actuator (after 20 sec of excitation).
Figure 5B:
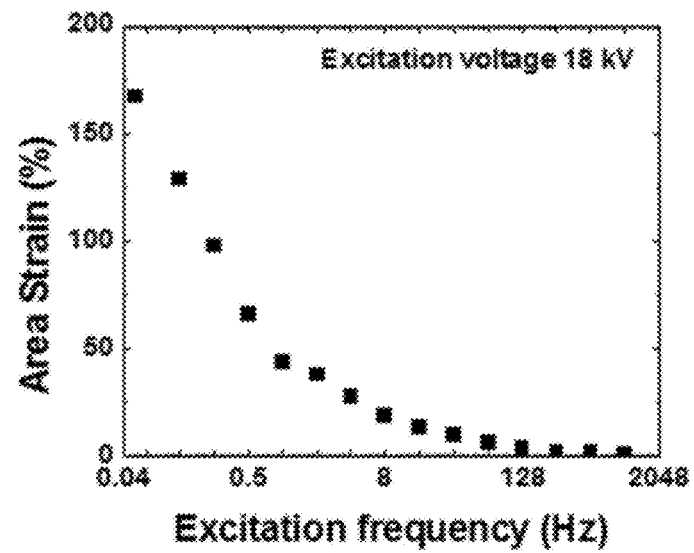
FIG. 5B is a plot of % strain area v. excitation frequency with 18 kV excitation.

The prestretch of VHB was fixed as λpre=3, and the ratio between radius of frame and radius of hydrogel was determined as κ=4. The thickness of 100 μm hydrogels which contains 2.74 M NaCl were attached on both top and bottom sides of VHB. On/off step voltage which is generated by a high voltage amplifier (Model 50/12, TREK) was applied to one side of hydrogel for 20 sec whereas the other electrode was grounded, and the area expansion of hydrogel was recorded. Under an applied voltage, the laminate deforms and reaches an equilibrium stretch λ. The areal strain is defined as $\varepsilon_{area}=(\lambda/\lambda_{pre})^2-1$, where $\lambda_{pre}$ is the pre-stretch of the laminate. As shown in FIGS. 5A and 5B, the artificial heart can be actuated up to 145% area strain without electrochemical reactions. Additionally, the artificial heart is fully transparent for the spectral range of visible light, and doesn't show light scattering even after large area expansion ≈145%. The high transmittance without scattering at high strain differentiates hydrogel electrolyte from carbon nanotube (CNT) based electrodes, since CNT based electrodes show blurred background at high strain due to the increased scattering of light.

Figure 5C:
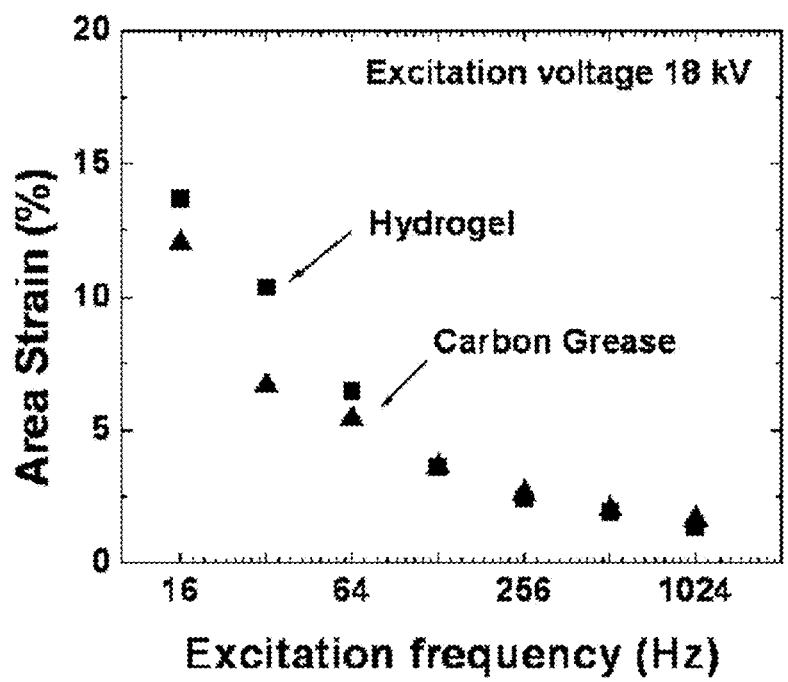
FIG. 5C provides a comparison of performance of actuators made using carbon grease as conductors with hydrogel electrolyte-based actuators according to one or more embodiments, shown in the plot of % strain vs. excitation frequency.

Actuators were also made using carbon grease as conductors. The actuators were subject to cyclic voltage, and the area strains were recorded. This response of the actuators using carbon grease as the conductor is nearly indistinguishable from that of actuators using the hydrogel as the conductor, as is shown in the plot of % strain vs. excitation frequency in FIG. 5C. Of course, the transparency of the carbon grease based actuator is far poorer than the transparent hydrogel electrode-based actuators.

Example 4. Performance, Transmittance and Resistivity 3 layers of VHB 4910 with Prestretch $\lambda_{pre}$=3, radius ratio κ=4, and 100 μm thick hydrogels which contain 2.74 M NaCl were used for a circular shape DE actuator. The actuated area of circular shape DE actuator with various on/off voltages after 20 sec excitation was plotted in FIG. 5A. Since the actuator shows time dependent area expansion, the area expansion was measured after reaching steady state of expansion. In FIG. 5A, a maximum of 167% area strain was achieved with 18 kV voltage which is corresponding to 144 MV/m applied electric field. Since the hydrogel is very compliant, the elasticity of the hydrogel doesn't limit the performance of the actuator much. Therefore, the maximum area strain which was achieved with solid state hydrogel electrolyte is very similar to that with liquid state electrode such as carbon grease electrode (i.e. 158% area strain was reported for carbon grease DE actuator with $\lambda_{pre}$=4 VHB at 412 MV/m applied electric field.

The area strain as a function of excitation frequency with 18 kV excitation voltage was plotted in FIG. 5B. On/off step voltages with various excitation frequencies in the range of 0.05 to 1024 Hz were applied, and movies were recorded with a high-speed camera (Vision Research Phantom V310) with frame rates between 1000 frames per second up to 3200 frames per second. The maximum and minimum areas of hydrogel were measured after enough cycles to get steady state values. The actuator with ionic conductors as electrodes continues to produce optically visible area expansion up to 1024 Hz. Beyond 1024 Hz, the experiments were not recorded optically because area expansion was not visible in the high speed videos. However, as is obvious from the additional loud speaker application in FIG. 7, the ionic conductors are still working even at 20K Hz.

Optical transmission spectra of hydrogel were recorded using a spectrophotometer (DU530, Beckman) with quartz cuvettes for the whole range of visible light. A quartz cuvette with pure water (≈99.99% transmittance at 550 nm) was used as a reference to reduce the reflection from index mismatch. As shown in FIG. 6A, transmittance spectra of the 11 mm thick hydrogel which contains 5.48 M NaCl show 98.94% total transmittance in the visible range. The electrical resistivity of hydrogel was measured as a function of uniaxial tensile stretch by using 4 point resistance measurement. To minimize electrochemical influences in the results, the resistance was measured with three relatively high measurement voltages (20~50 V) and the corresponding currents after saturation. The resistivities of salty water with 1.37, 2.74 and 5.48 M NaCl concentrations were plotted in FIG. 6B as dashed lines. Resistivity of 0.053, 0.02967 and 0.01827 Ωm were obtained for 1.37, 2.74 and 5.48 M NaCl concentration, respectively. The average molar conductivity 120.19 S-cm$^2$/mol was calculated from the resistivity for salty water, and by comparing it with the reported value 118.5 Scm$^2$/mol, the reliability of resistance measurement was confirmed. Electrical resistivity of the hydrogels which have same concentrations of NaCl was compared with the resistivity of salty water as a function of uniaxial tensile stretch in FIG. 6B. Hydrogels show almost identical electrical resistivity with salty water which has the same concentration of NaCl when they are not stretched.

Figure 6C:
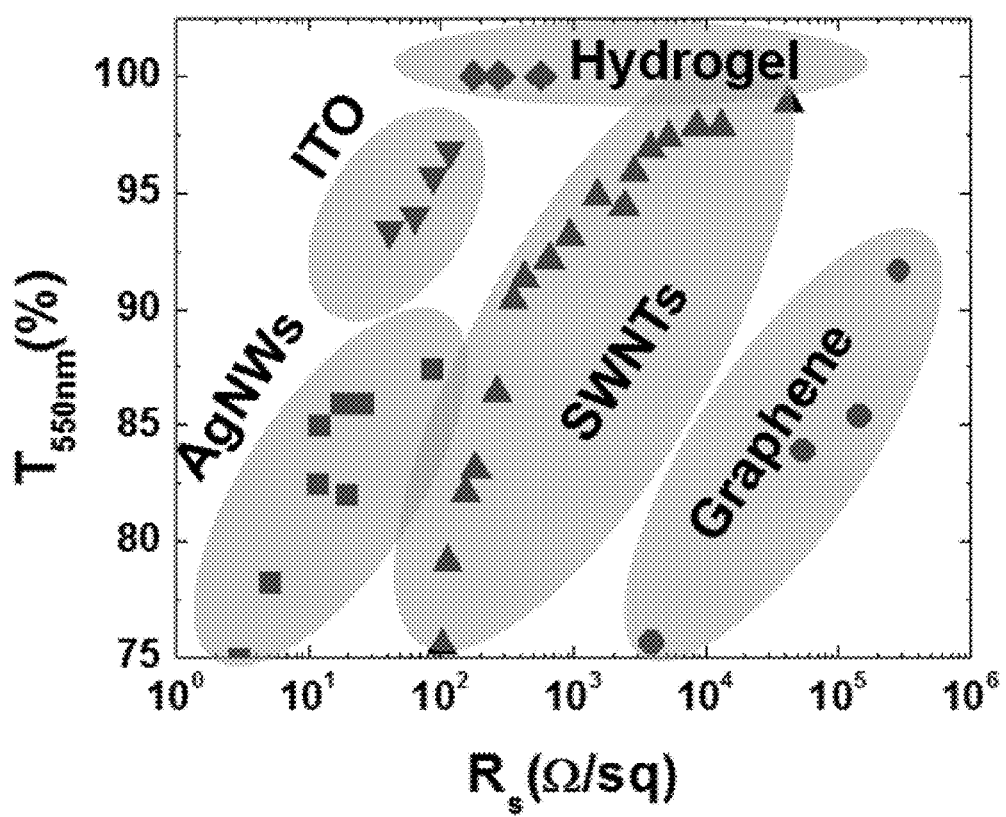
FIG. 6C is a plot of % transmittance at 550 nm vs. sheet resistance for a variety of materials.
Figure 6D:
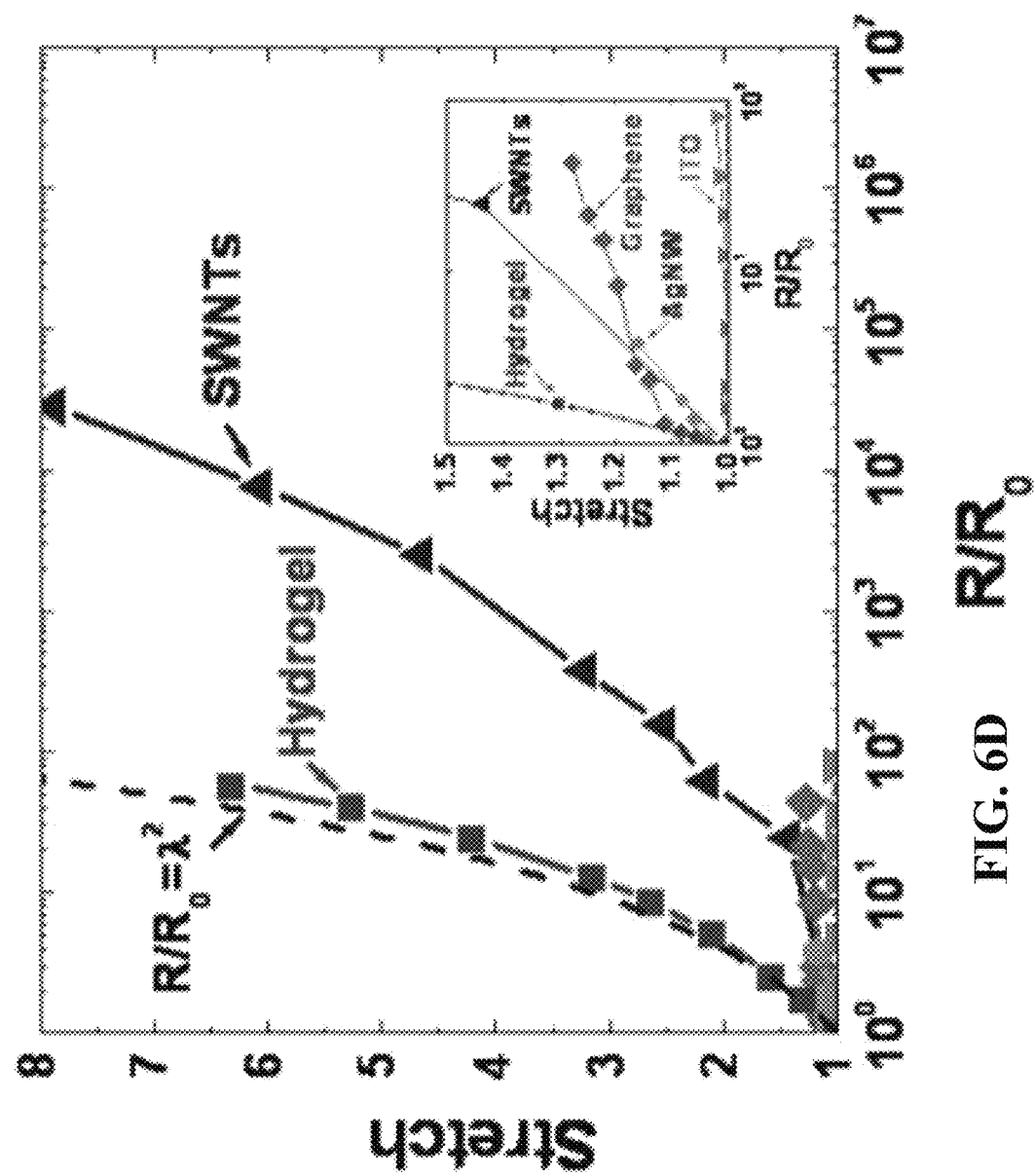
FIG. 6D is a plot of stretch against normalized resistance (normalized against resistance in the non-stretched state) for a variety of conductive materials; inset is an exploded view of stretch between 1 and 1.5 showing responses for ITO, graphene and silver nanowires.

The sheet resistance, transmittance, and stretchability of the hydrogel electrolyte are compared in FIGS. 6C and 6D with other stretchable electrodes reported in the literature employing various conducting materials such as silver nanowires (AgNWs), single-wall carbon nanotubes (SWNTs), graphene, and indium tin oxide (ITO). Hydrogel electrolyte shows best performance in terms of the transmittances of visible light, and its transmittance was not decreased at all when more ions were added to reduce the sheet resistance. However, since the solubility of ions will limit the minimum sheet resistance of electrolyte, ITO and AgNWs show lower sheet resistance than hydrogel electrolyte at room temperature. As shown in FIG. 6D hydrogel electrolyte will provide more stable and predictable resistance under stretched condition than other stretchable electrodes. For instance, when SWNTs on VHB were stretched, the electrical resistance of the whole electrode will increase rapidly by the separation of nanotubes. However, because the ions in hydrogel are distributed uniformly, the electrical resistance of the hydrogel electrolyte will follow the prediction of geometrical deformation even at high stretch as shown in FIG. 6D.

Example 5. Transparent Loudspeaker

Ionic conduction is often appraised to be very slow. While signal speed in electronic conductors is without doubt much faster in comparison, electrical nerve impulses in mammals are based on ionic conduction and reach surprisingly fast speeds in excess of 100 m/s.

Figure 7A:
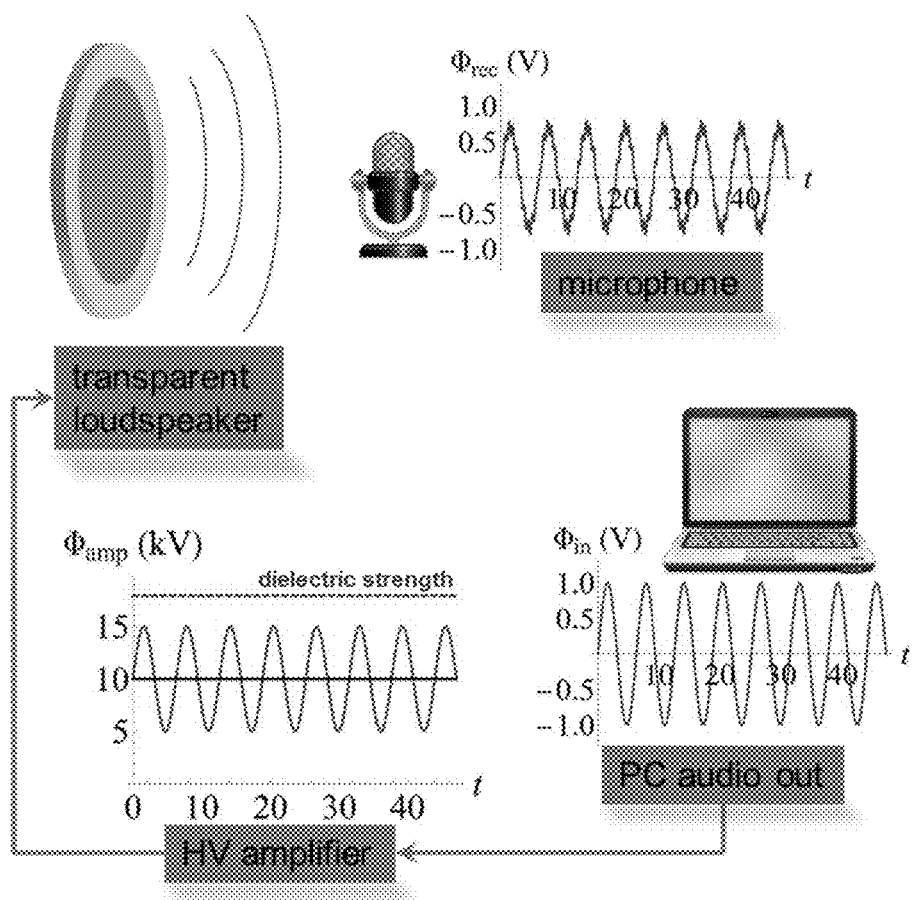
FIG. 7A is a schematic illustration of a transparent loudspeaker capable of reproducing sound across the whole human hearing range from 20 Hz to 20 kHz in which the voltage signal of a PC audio output is amplified by a high voltage amplifier, which also adds a DC offset to prevent frequency doubling and to make best use of the dynamic range of the electromechanical system, and a microphone records the produced sound.
Figure 7B:
FIG. 7B is a photo of the loudspeaker in front of a laptop screen playing music from YouTube.

To demonstrate the high speed capability of ionic conductors in electromechanical transducers a fully transparent elastomeric membrane loudspeaker, as shown in FIGS. 7A-7D, was prepared. Similar to the heart transducer, three layers of 3M™ VHB™ 4910 acrylic elastomer tape were prestretched onto a circular acrylic frame with $\lambda_{pre}=3$ and a radius ratio of $\kappa=2$. Circular hydrogel electrodes sandwiching the VHB membranes were fabricated with a thickness of 100 μm and a diameter of 10 cm. FIG. 7A shows the operational principle of the loudspeaker. The analog electrical sound signal from a PC audio output is fed to a suitable high voltage amplifier (TREK, model 30/20A; fixed 3000 V/V gain; slew rate larger than 750 V/μs). The high voltage amplifier is also programmed to add a 12.5 kV DC offset, to prevent frequency doubling (the Maxwell Stress deforming the elastomer is quadratic in voltage, so changes of positive to negative polarity have to be avoided) and to shift the time-varying signal up in the region of most efficient electromechanical coupling (into the region just below the dielectric strength limit of the elastomer membrane). This high voltage signal is applied to the hydrogel electrodes and a webcam with a microphone (Logitech, QuickCam® Pro 9000) records the scene from 15 cm distance, see FIG. 7B. To illustrate the fully transparent design the loudspeaker membrane was placed between a laptop screen and the webcam and the loudspeaker was able to play music from the web. The sound produced from the transparent loudspeaker is clearly audible from 5 m distance.

Figure 7C:
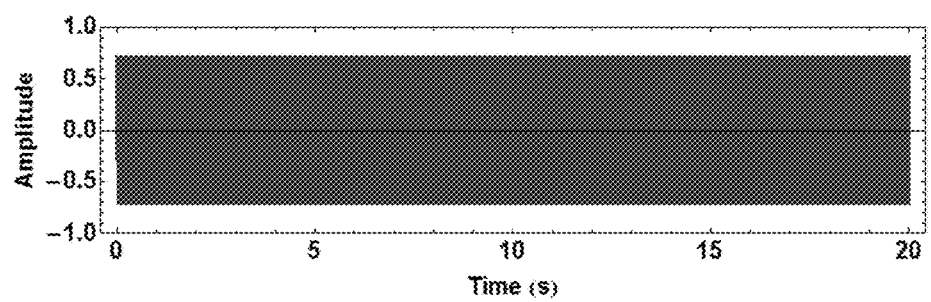
FIG. 7C is a plot showing amplitude variation with time of a 20 s test sound (full spectrum (20 Hz-20 kHz) linear sine sweep).
Figure 7D:
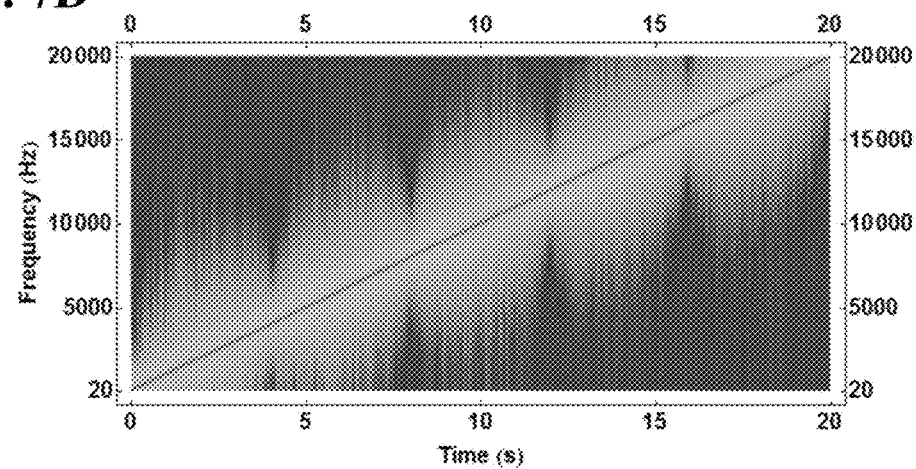
FIG. 7D is a spectrogram of the test sound displaying the scan through all audible frequencies
Figure 7E:
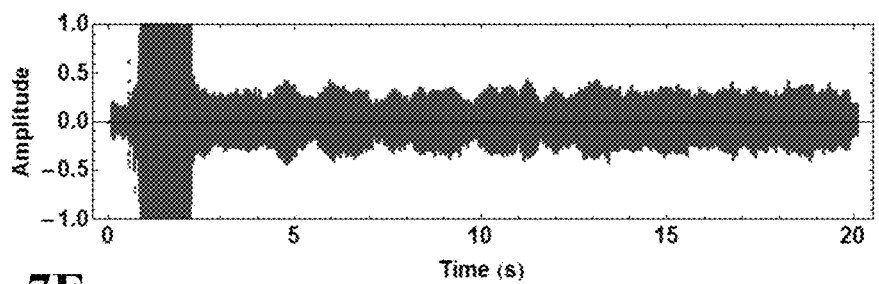
FIG. 7E shows amplitude variation with time of the recorded sound; in the lower frequency range some resonances emerge, characterized by the amplitude peak between second 1 and 2.
Figure 7F:
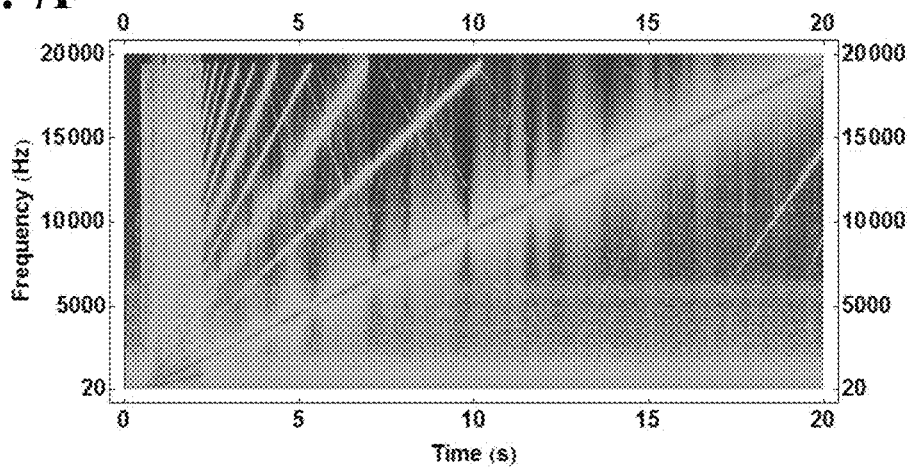
FIG. 7F is a spectrogram of the recorded sound showing the successful reproduction of frequencies throughout the whole audible spectrum, and higher harmonics and noise emerging from the resonances.

To test the sound reproduction fidelity, frequency range and resonance behavior of the loudspeaker in more detail, we used a test sound from www.audiocheck.net/testtones_s-inesweep20-20k.php, a linear sine sweep from 20 Hz to 20 kHz within 20 s and with constant amplitude. FIG. 7C shows the amplitude variation with time of the original test sound WAV file. FIG. 7D shows the spectrogram of the original sound file. The spectrogram displays the scan through the whole audible frequency range (the rainbow color coding shows the intensity distribution of frequencies as a function of time; warmer colors indicate higher intensity; the frequency spectrum for each specific point in time of the test sound was obtained by short-time Fourier transform of the WAV signal). The amplitude variation with time of the sound recorded with the webcam is shown in FIG. 7E. In the region between second 1 and 2 of the recording the amplitude peak indicates resonances, but the remainder of the recording is characterized by only small amplitude variations. The resonances are mainly present in the low frequency regime and originate from the simple frame construction of the loudspeaker which was not optimized for resonance suppression. FIG. 7F clearly proves the high speed capability of the hydrogel electrodes based on ionic conduction. The spectrogram of the recorded sound displays the successful reproduction of the main signal of the original test sound throughout the audible frequency range all the way up to 20 kHz. Also visible are the above mentioned resonances between second 1 and 2 (visible as noise distributed across a large frequency range) together with low frequency background noise from the high voltage generator and the higher harmonics of the frequency sweep.

The demonstrated transparent loudspeaker was mainly designed to illustrate the combination of two attributes: large frequency bandwidth of an electromechanical transducer based on ionic conduction paired with very high transparency. To use transparent all elastomer loudspeakers based on the above principle for commercial applications (e.g. in front of screens or placed on windows) the resonance behavior can be optimized by special frame constructions or alternative geometries (probably also spherical designs are useful). Lowering the membrane thicknesses and using multilayer systems will bring the required driving voltage levels down to realistic numbers.

Example 6. Strain Sensor in Equibiaxial Mode

A fully transparent capacitive strain sensor that can be subject to equibiaxial strain was demonstrated using hydrogel electrolyte in the device shown in FIGS. 8A-8B. FIG. 8C shows a specific design of strain sensor. 100 μm thick hydrogels which contain 2.74 M NaCl were stacked on both top and bottom sides of a layer of VHB 4905 elastomer resulting in a configuration similar to a parallel-plate capacitor. To prevent the evaporation of water, one more layer of VHB was added on both top and bottom side—a form of semi-encapsulation that helps reduce water loss. An equibiaxial stretcher 800 was made of 3 mm thick acrylic cut into the wheel and spokes design shape by using laser cutting system. When the round shaft 810 is rotated, the rotation is transferred to an arm 820 through a gear 830. Since the rotation of the mobile frame makes the same amount of movement to all twelve arms, the rotation causes equibiaxial stretching. FIG. 8A shows the device in a relaxed unstretched state, while FIG. 8B shows the device in an expanded stretched state.

Figure 8D:
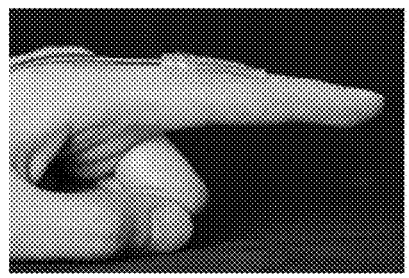
FIGS. 8D-8F provide photographs of transparent strain sensor glued on a finger (D) before and (E) after bending and (F) the front view of strain sensor on bent finger demonstrates the transparency of the strain sensor.
Figure 8E:
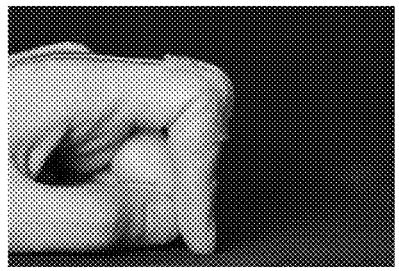
Figure 8F:
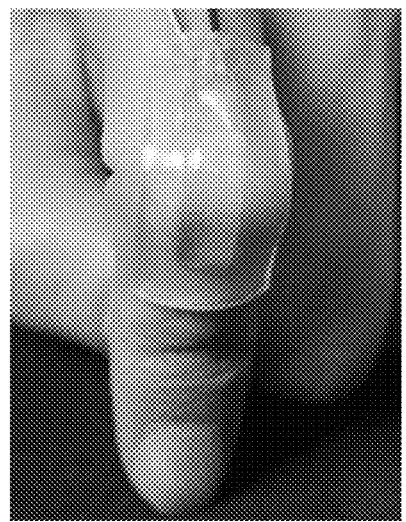
Figure 8G:
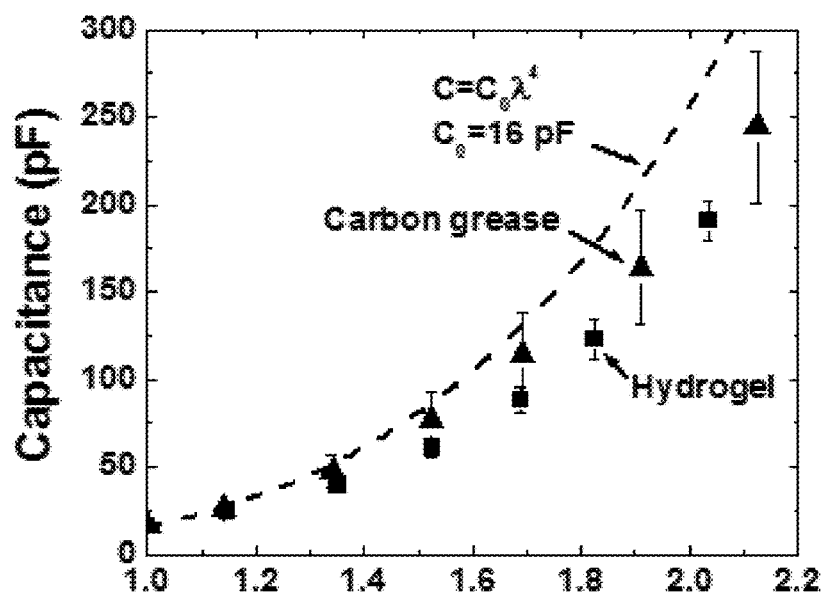
FIG. 8G is the capacitance of hydrogel capacitor measured as a function of equibiaxial stretch and compared with same size of carbon grease capacitor.

The capacitance of the hydrogel strain sensor was measured as a function of equibiaxial stretch and compared to a capacitive strain sensor with carbon grease electrodes of equal size, see FIG. 8G. Proportional capacitance was observed for both hydrogel and carbon grease strain sensors by increasing stretch, and the strain sensors show good agreement. At high stretch, the measured capacitances of the strain sensors are slightly lower than the theoretical prediction $C=C_0\lambda^4$ (dashed line), which only takes account of geometrical change.

Example 7. Strain Sensor in Uniaxial Mode

Figure 11A:
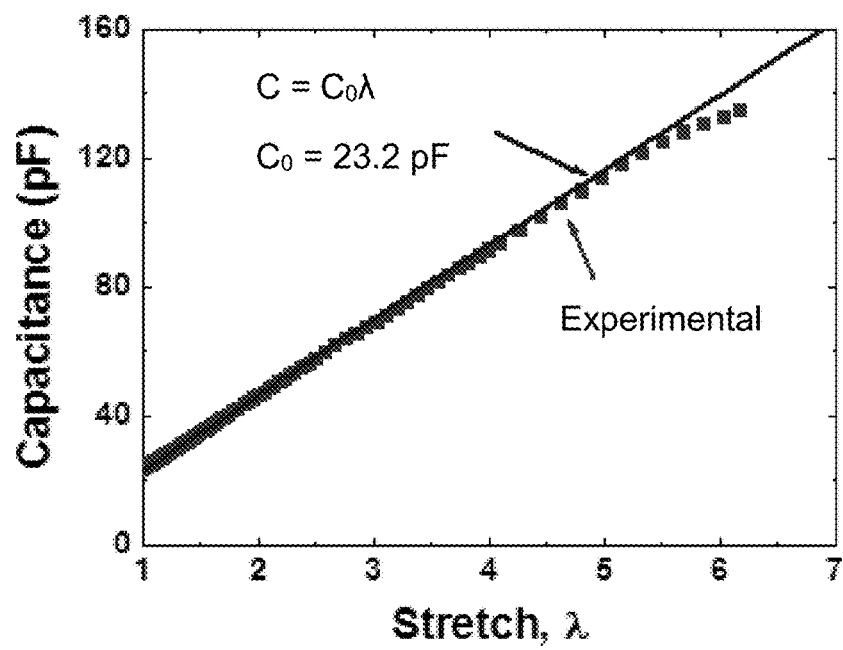
FIG. 11A is a plot of capacitance (pF) vs. stretch for a uniaxially stretched sensor according to one or more embodiments, in which the stretch $\lambda$ is the distance between two clamped edges when the sensor is deformed divided by the distance when the strip is undeformed.
Figure 11B:
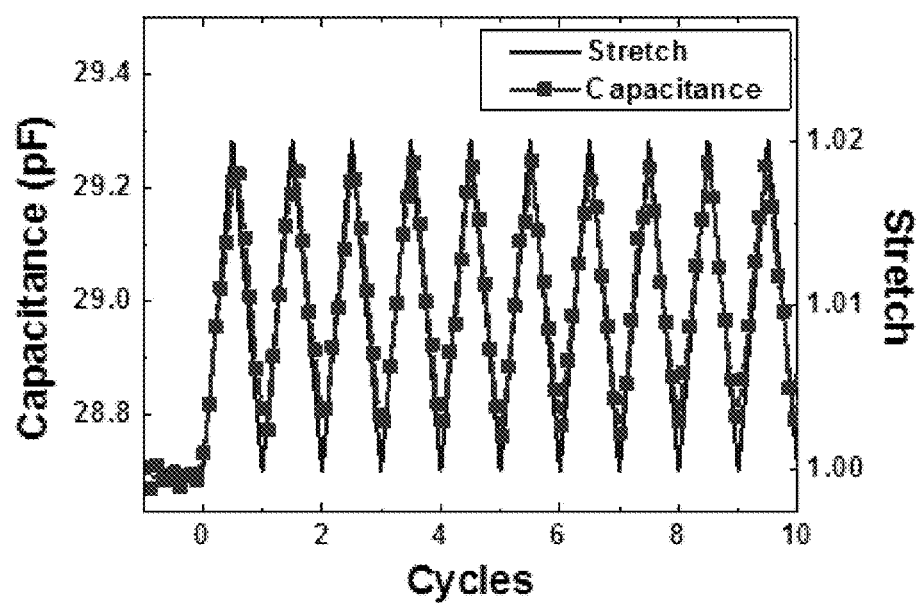
FIG. 11B illustrates the change in capacitance for a uniaxially stretched sensor according to one or more embodiments when the sensor was cyclically loaded at a frequency of 1 Hz and a maximum stretch of 1.02.

The ionic strain sensor was tested in uniaxial mode. A strip of ionic sensor prepared as shown in FIG. 8C was secured at each end between acrylic plates, and stretched using a mechanical testing apparatus (Instron, Model 3342) with a 50N load cell at a rate of 0.5/min. The capacitance of the ionic skin was measured using a capacitance meter (Agilent, E4980A) with a voltage of 1 V at a frequency of 20 kHz. The ionic skin could be stretched to about six times the initial length of the strip. The experimentally measured capacitance increased linearly with the stretch, and matched well with the theoretical prediction, $C=C_0\lambda$, as is shown in FIG. 11A. The ionic skin was also stretched by cyclic uniaxial force at a frequency of 1 Hz and a maximum strain of 2%. The change in capacitance within each cycle was stable and is shown in FIG. 11B.

Example 8. Strain Sensor for Use as an Ionic Skin Sensor

Hydrogel electrolyte shows high transmittances of visible light, and provides a stable and predictable resistance under stretched conditions. Strain sensors based on hydrogel electrodes offer superior performance. A fully transparent capacitive strain sensor was demonstrated using hydrogel electrolyte.

FIG. 8C shows a specific design of strain sensor that can be placed on a finger. 100 μm thick hydrogels which contain 2.74 M NaCl were stacked on both top and bottom sides of a layer of VHB 4905 elastomer resulting in a configuration similar to a parallel-plate capacitor. To prevent the evaporation of water and to glue the strain sensor to the finger, one more layer of VHB was added on both top and bottom side—a form of semi-encapsulation that helps reduce water loss. In addition, VHB is marketed as a double-sided adhesive tape, one side of which was used to adhere the sensor to the finger. Photographs of the transparent strain sensor glued on a finger before and after bending are also shown in FIGS. 8D-8E, respectively. When the finger bent, the joint of the finger became a non-developable surface, but the ionic skin stretched and conformed to the movement of the joint. The adhesion between the ionic skin and the finger was adequate: no debonding occurred as the finger bent repeatedly. As shown in FIG. 8F, the front view of the strain sensor on a bent finger demonstrates excellent transparency of the strain sensor.

Figure 8H:
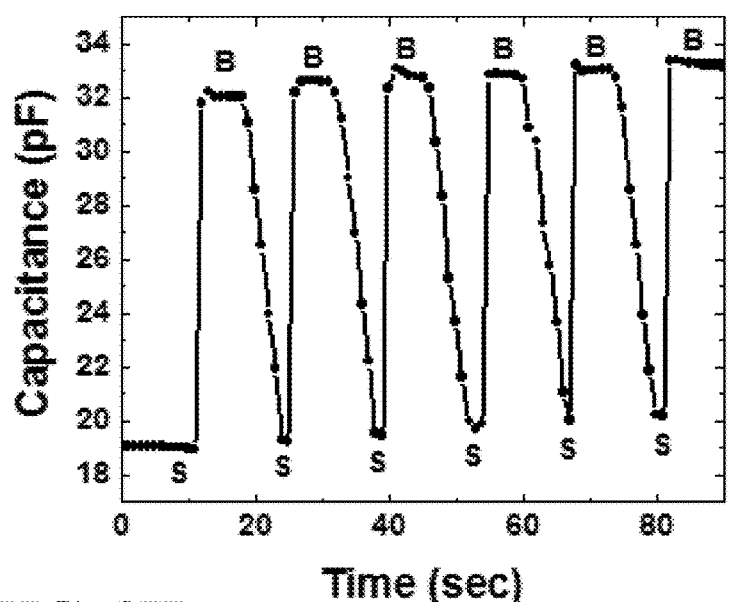
FIG. 8H is the capacitance change of hydrogel strain sensor with multiple cycles of finger bending ('B' and 'S' denote bent and straight, respectively).

Metal wires connected to the two hydrogel layers were used to measure capacitance. As the finger bent repeatedly, the capacitance of the ionic sensor was recorded. The capacitance of the strain sensor was measured by a capacitance meter (LCR/ESR meter Model 885, BK precision) with a 1V and 100 Hz alternating current test signal. FIG. 8H plots the capacitance change of the hydrogel strain sensor with 6 cycles of finger bending, showing stable response of the strain sensor.

Example 9. Pressure Sensor

The ionic electrode can be incorporated into devices to readily function as a pressure sensor.

Figure 12A:
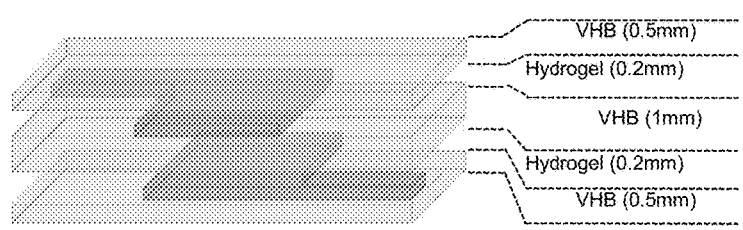
FIGS. 12A and 12B provide a (a) schematic and (b) photographic depiction of a pressure sensor according to one or more embodiments.

A pressure sensor of dimensions 10×10×2.6 mm$^3$ was prepared using a design similar to that of a strain sensor, using a hydrogel/VHB dielectric/hydrogel stack sandwiched between two VHB sheets to reduce water loss. See, FIG. 8C and FIG. 12A.

Figure 12B:
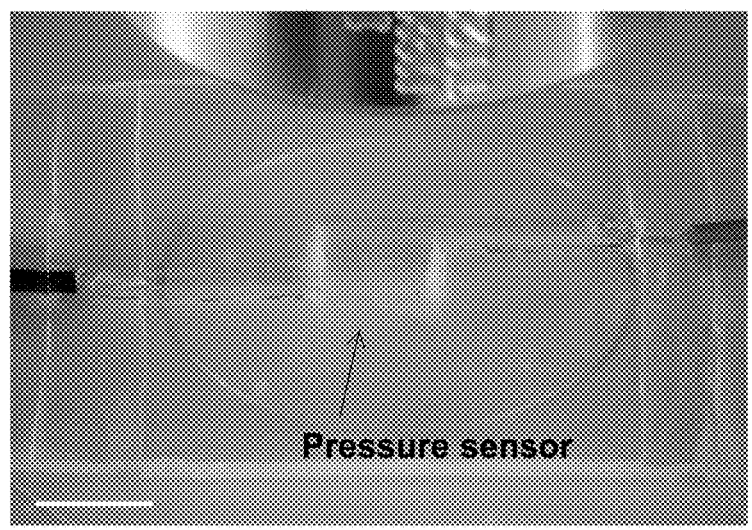
Figure 12C:
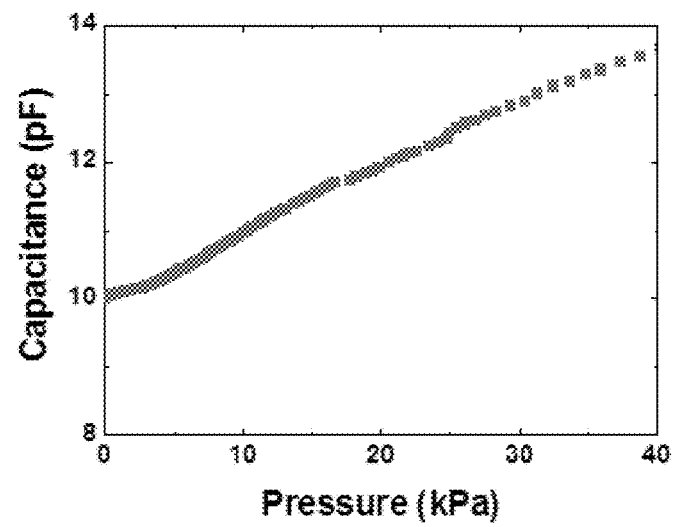
FIG. 12C is a plot of capacitance (pF) vs. pressure (kPa) for a pressure sensor according to one or more embodiments; inset is an expanded plot for up to 1 kPa applied pressure, illustrating the high sensitivity of the device.

The pressure sensor was placed between two grounded metal stages, and a small amount of mineral oil was applied on the surfaces of the sensor to reduce the adhesion and friction between the sensor and the stages, as shown in the photograph in FIG. 12B. As the mechanical testing apparatus compressed the sensor at a strain rate of 0.5/min, the capacitance of the sensor was measured. The two layers of the hydrogel raised the height of the pressure sensor relative to the surrounding elastomer, so that the testing machine applied the force on the pressure sensor. As the pressure sensor was compressed in thickness, its area expanded. The pressure was defined as the applied force divided by the area of the undeformed dielectric elastomer. The pressure sensor demonstrated a significant change in capacitance in response to applied pressure, as shown in a plot of capacitance vs. pressure in FIG. 12C. The capacitance response was quite sensitive, demonstrating a measurable response for even small pressure forces, e.g., about 10 kPa which can be applied by the touch of a finger.

Figure 12D:
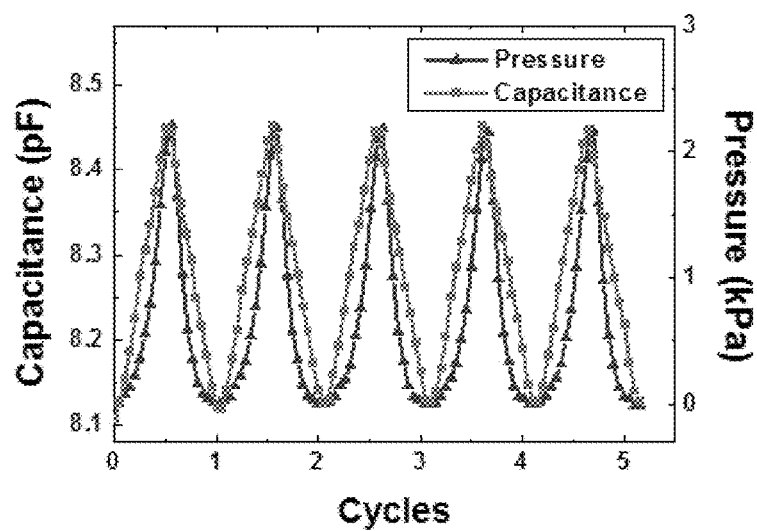
FIG. 12D is a plot of capacitance (pF) and pressure (kPa) over several cycles for a pressure sensor according to one or more embodiments.
Figure 12E:
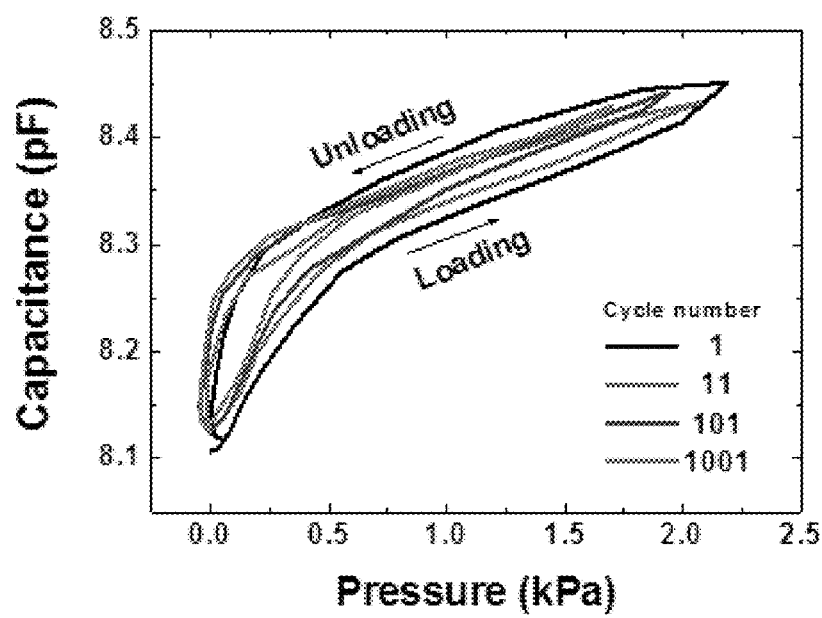
FIG. 12E shows capacitance-pressure curves for 4 representative cycles (cycles 1, 11, 101 and 1001) according to one or more embodiments.

The pressure sensor was also compressed repeatedly with a prescribed maximum strain of 1% at a frequency 0.5 Hz, while the capacitance and pressure were recorded. A plot of pressure and capacitance change during cycling is shown in FIG. 12D. The capacitance-pressure curves were stable over cycles. The relative change in capacitance was less than 0.2% through 1000 cycles, as is demonstrated in the capacitance-pressure curves for 4 representative cycles (cycles 1, 11, 101 and 1001) shown in FIG. 12E.

Example 10. Pressure Sensor with Location Sensitivity

The ionic pressure sensor readily resolves the pressure of a gentle touch of a finger (~10 kPa).

A transparent and wearable touchpad, consisting of four pressure sensors over a single large layer of grounded hydrogel was prepared. The transparent touchpad includes four individual pressure sensors which share a common layer of hydrogel; however, the design still employs the same five-layer design of dielectric-ionic conductor-dielectric-ionic conductor-dielectric.

Figure 13A:
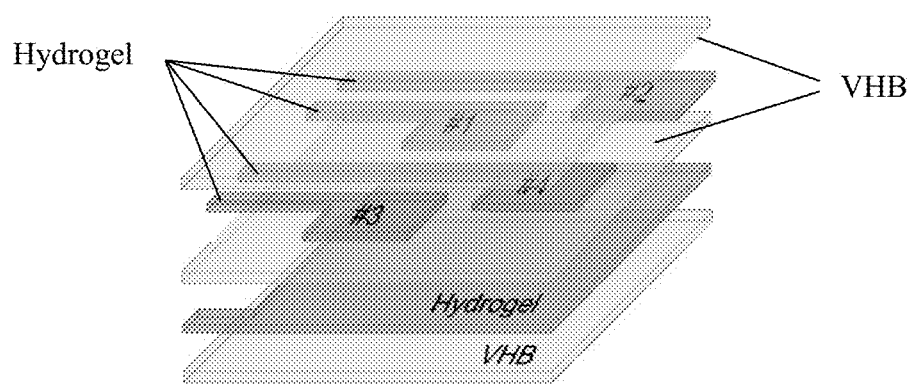
FIG. 13A is an exploded perspective view of a pressure-sensitive touchpad having four pressure buttons according to one or more embodiments.
Figure 13B:
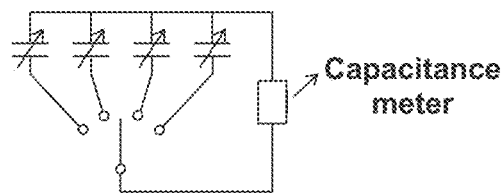
FIG. 13B is a circuitry schematic showing connection of the four touchpads to a capacitance meter through a rotational switch.

The present design, which employs a manually operated rotational switch was used for simplicity and to demonstrate the principle. As seen in FIG. 13A, the four top layers of hydrogel form four individual pressure sensitive buttons, where for simplicity the bottom hydrogel layers are joint together into one single piece with identical electric potential (grounded in the device). The four pressure sensors can be read out individually. The four top layers of hydrogel are connected to a rotational switch, which depending on the rotational position connects hydrogel #1, #2, #3 or #4 to an external capacitance meter. The schematic for the touchpad is shown in FIG. 13B. For each position the large bottom layer of hydrogel is connected, but only the area which overlaps with the active top layer of hydrogel contributes towards the measured capacitance. In a practical device, the number of pressure sensitive pixels can be much larger and specifically designed electrical readout circuits would be used.

Figure 13C:
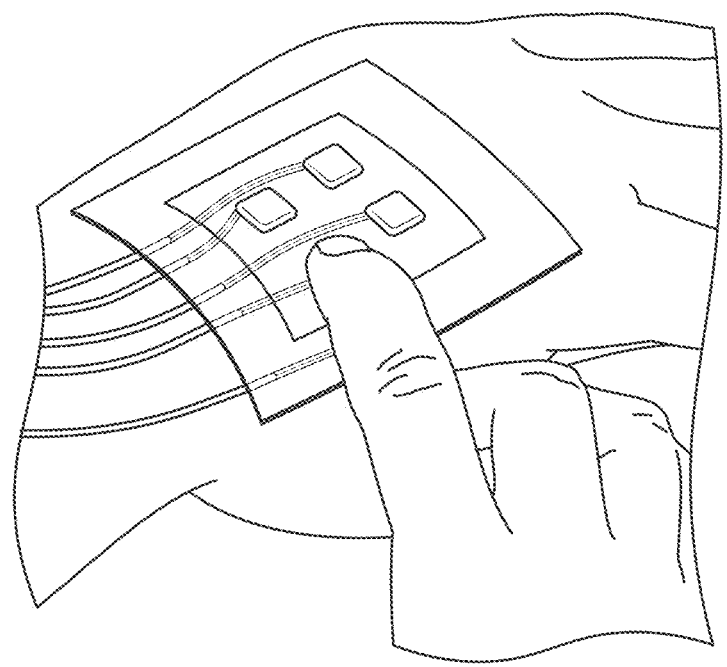
FIG. 13C is a photograph of the touchpad attached to a hand and demonstrating the touchpad feature.
Figure 13D:
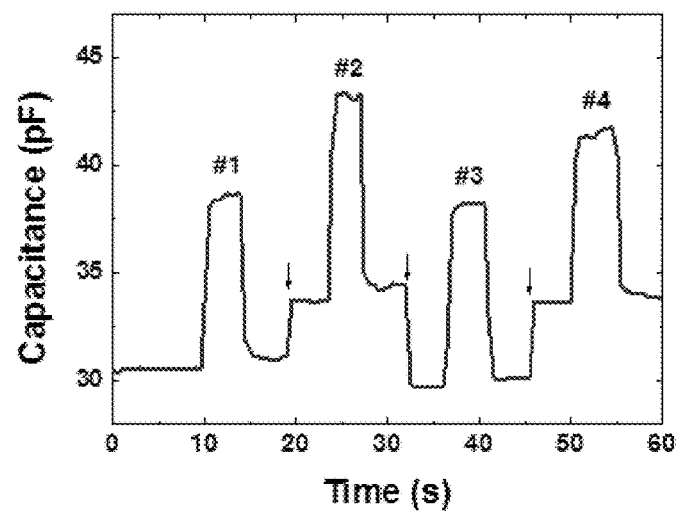
FIG. 13D is a plot of capacitance (pF) vs. time (s) showing response to finger pressure for each of the buttons in the touchpad of FIG. 13C; the numbers indicate different buttons being pressed and the arrows mark the times at which the rotation switch was turned to the next position.
Figure 13E:
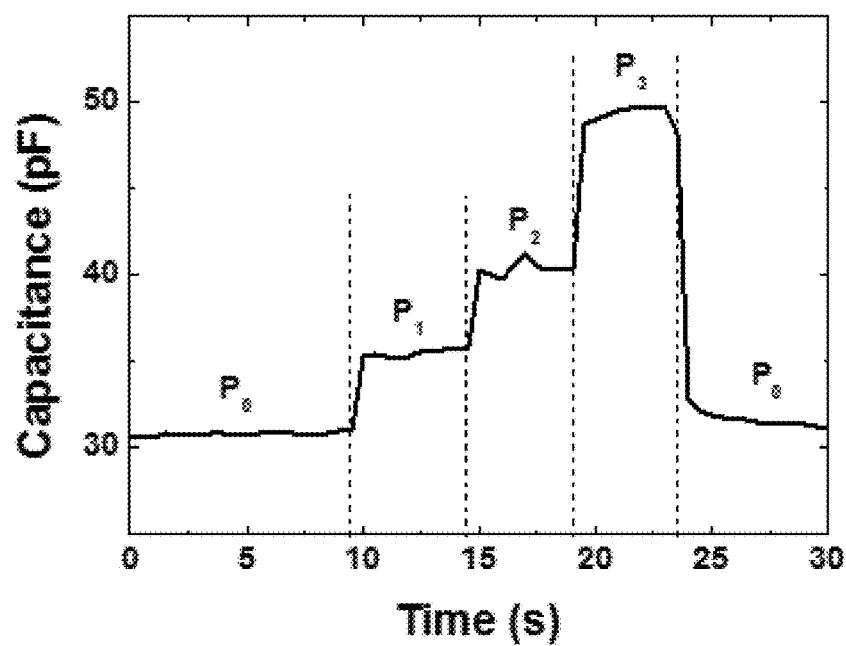
FIG. 13E is a plot of capacitance (pF) vs. time (s) showing stepwise capacitive response to stepwise increase in pressure.

The capacitance was recorded through a Labview (National Instruments) program. The touchpad was attached on the back of a hand, and buttons were pressed with a finger as demonstrated in the photograph of FIG. 13C. In the capacitance-time plot shown in FIG. 13D, the numbers indicate buttons, and the arrows indicate the times of switching. During the time each button was pressed, the capacitance remained nearly a constant. In this design, the dielectric between the ground hydrogel and the interconnect hydrogel also contributed to the initial values of capacitance. Because button 2 and 4 have longer interconnects than button 1 and 3, the initial capacitances of button 2 and 4 are larger than those of button 1 and 3. When a finger applied gentle, intermediate and large pressures, and then removed, the capacitance changed accordingly, as demonstrated in the capacitance-time plot shown in FIG. 13E. Whereas an on/off button expresses only two states, a button in our touchpad senses the levels of pressure and expresses multiple outputs.

Example 11. Ionic Liquid Electrolytes

Ionic liquids can be used as conductors for high-speed, large-strain dielectric elastomer actuators or interconnects.

Figure 9A:
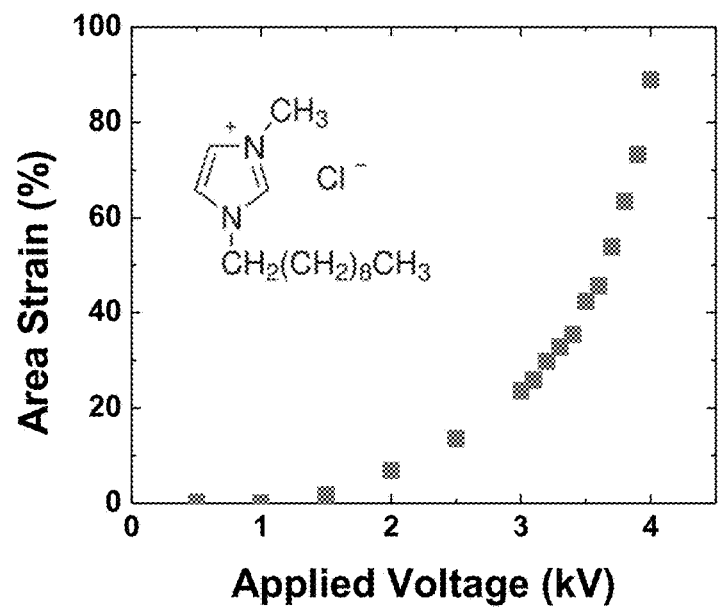
FIGS. 9A and 9B demonstrate the performance of a dielectric elastomer actuator using an ionic liquid as the conductor and provides a plot of (A) Area strain of an actuator using the ionic liquid [$C_{10}$MIM][Cl] as conductor as a function of applied voltage, and (B) area strain measured as a function of excitation frequency at an applied voltage of 4 kV.
Figure 9B:
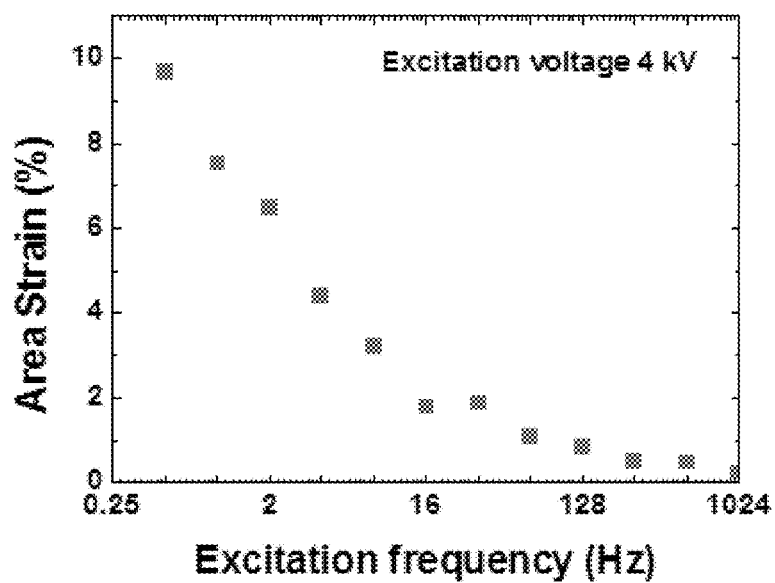

An actuator was built using a commercially available ionic liquid 1-Decyl-3-methylimidazolium chloride, [$C_{10}$MIM][Cl]. One layer of VHB 4910 was stretched to three times the initial radius and fixed to a circular rigid acrylic frame of diameter 12 cm. The ionic liquid was painted to the two faces of the dielectric elastomer within circular regions of diameter 3 cm. On each face, a line of the ionic liquid was also painted from the circular region to the acrylic frame, where the line was connected to a copper electrode. When a step voltage was applied, the actuator expanded gradually. The area strain at 20 s after the voltage is applied is plotted as a function of the magnitude of the voltage as shown in FIG. 9A. When a cyclic voltage was applied, the steady area strain was recorded as a function of the frequency, which is reported in FIG. 9B. Both characteristics are comparable to those observed for actuators using carbon grease as conductors.

The RC delay of the actuator using the ionic liquid as the conductor remains exceedingly small, so that the frequency of actuation is not limited by the electrical resistance of the ionic liquid, but by the mechanical inertia. Assuming representative values for the thickness $H\sim 10^{-3}$ m and resistivity $\rho\sim 10$ $\Omega$m of the ionic liquid, the sheet resistance is estimated to be $R=10^4$ $\Omega$/sq. Even though the sheet resistance of the ionic liquid is two orders of magnitudes higher than that of the ionic hydrogels, high-speed actuation is nevertheless readily achieved.

Although the present disclosure has been described and illustrated in the foregoing example embodiments, it is understood that the present disclosure has been made only by way of example, and that numerous changes in the details of implementation of the disclosure may be made without departing from the spirit and scope of the disclosure, which is limited only by the claims which follow. Other embodiments are within the following claims.

What is claimed is:

1. An electrode comprising:
   an ionic electrode;
   at least an external signal and
   a dielectric layer comprising an elastomer,
   wherein the ionic electrode is capacitively coupled with the external signal by the dielectric layer.

2. The electrode of claim 1, wherein the ionic electrode further comprises an ionic electrolyte; wherein the ionic electrolyte comprises an elastomer or electroactive polymer and an electrolyte dispersed throughout the elastomer or electroactive polymer to provide a transparent electrolyte.

3. The electrode of claim 2, wherein the electrolyte layer elastomer comprises a hydrogel or a lyogel.

4. The electrode of claim 2, wherein the electrolyte comprises an aqueous salt solution.

5. The electrode of claim 4, wherein aqueous salt solution comprises a deliquescent salt.

6. The electrode of claim 4, wherein the aqueous salt solution has a salt concentration in the range of fully saturated to isotonic in physiological systems.

7. The electrode of claim 6, wherein the physiological systems are cells.

8. The electrode of claim 2, wherein the electrolyte comprises an ionic liquid.

9. The electrode of claim 8, wherein the ionic liquid forms a liquid layer.

10. The electrode of claim 9, wherein the liquid layer is confined within boundaries to prevent flow.

11. The electrode of claim 8, wherein an elastomer is swollen with the ionic liquid to provide an elastomeric ionic electrode.

12. The electrode of claim 2, wherein the electrolyte further comprises a humectant.

13. The electrode of claim 2, wherein electrolyte solution has a minimum resistivity of 0.02 Ohm-meter.

14. The electrode of claim 2, wherein the electrolyte has a transmittance of greater than 95%.

15. The electrode of claim 2, further comprising electrical connectors in electrical contact with the transparent electrolyte for connection to an electronic circuit.

16. The electrode of claim 1, wherein the dielectric layer is transparent.

17. The electrode of claim 16, wherein the dielectric layer is elastomeric.

18. The electrode of claim 16, wherein the dielectric layer is an electroactive polymer.

19. The electrode of claim 16, wherein the dielectric layer is biodegradable or biocompatible.

20. The electrode of claim 18, wherein the electroactive polymer is a piezoelectric polymer.

21. The electrode of claim 1, wherein the electrode is stretchable.

22. The electrode of claim 1, wherein the electrode is biodegradable or biocompatible.

23. The electrode of claim 1, wherein the electrode is encapsulated to reduce loss of electrolyte.

24. The electrode of claim 1, wherein the electrode is configured as a stretchable wire or interconnect for use in circuits.

* * * * *